United States Patent
Pagano et al.

(10) Patent No.: US 8,263,387 B2
(45) Date of Patent: Sep. 11, 2012

(54) SHEATH FLOW DEVICES AND METHODS

(75) Inventors: Paul Pagano, Moorpark, CA (US); Yanting Zhang, Santa Barbara, CA (US); Jiangrong Karen Qian, Thousand Oaks, CA (US); Hyongsok Tom Soh, Santa Barbara, CA (US); Paul W. Dempsey, Studio City, CA (US); Andre' De Fusco, Westlake Village, CA (US)

(73) Assignee: Cynvenio Biosystems, Inc., Westlake, CA (US)

( * ) Notice: Subject to any disclaimer, the term of this patent is extended or adjusted under 35 U.S.C. 154(b) by 95 days.

(21) Appl. No.: 12/813,285

(22) Filed: Jun. 10, 2010

(65) Prior Publication Data

US 2011/0003303 A1    Jan. 6, 2011

Related U.S. Application Data

(60) Provisional application No. 61/313,625, filed on Mar. 12, 2010, provisional application No. 61/185,919, filed on Jun. 10, 2009.

(51) Int. Cl.
*C12M 1/00* (2006.01)
*G01N 15/06* (2006.01)

(52) U.S. Cl. ............ 435/283.1; 435/6.1; 435/288.2; 435/288.5; 422/68.1; 422/527

(58) Field of Classification Search .............. None
See application file for complete search history.

(56) References Cited

U.S. PATENT DOCUMENTS

| | | |
|---|---|---|
| 4,893,496 A | 1/1990 | Bau et al. |
| 5,108,933 A | 4/1992 | Liberti et al. |
| 5,186,827 A | 2/1993 | Liberti et al. |
| 5,200,084 A | 4/1993 | Liberti et al. |
| 5,466,574 A | 11/1995 | Liberti et al. |
| 5,622,831 A | 4/1997 | Liberti et al. |
| 5,646,001 A | 7/1997 | Terstappen et al. |
| 5,660,990 A | 8/1997 | Rao et al. |
| 5,795,470 A | 8/1998 | Wang et al. |
| 5,837,200 A | 11/1998 | Diessel et al. |
| 5,993,665 A | 11/1999 | Terstappen et al. |

(Continued)

FOREIGN PATENT DOCUMENTS

DE    102004040785    3/2006

(Continued)

OTHER PUBLICATIONS

Adams et al., "Multitarget Magnetic Activated Cell Sorter", PNAS, Nov. 25, 2008, vol. 105, No. 47, pp. 18165-18170.

(Continued)

*Primary Examiner* — Betty Forman
(74) *Attorney, Agent, or Firm* — Weaver Austin Villeneuve & Sampson, LLP

(57) ABSTRACT

The invention relates generally to fluid processing and, in particular aspects, processing fluids for detection, selection, trapping and/or sorting of particulate moieties. Sheath flow devices described allow isolation of target species from fluid samples while avoiding non-specific binding of unwanted species to the surfaces of the separation device. Biological fluid processing, detection, sorting or selection of cells, proteins, and nucleic acids is described. The invention finds particular use in diagnostic settings, analyzing a patient's medical condition, monitoring and/or adjusting a therapeutic regimen and producing cell based products.

50 Claims, 12 Drawing Sheets

U.S. PATENT DOCUMENTS

| | | | |
|---|---|---|---|
| 6,007,690 A | 12/1999 | Nelson et al. |
| 6,010,607 A | 1/2000 | Ramsey |
| 6,013,188 A | 1/2000 | Terstappen et al. |
| 6,250,475 B1 | 6/2001 | Kwasniewicz et al. |
| 6,432,630 B1 | 8/2002 | Blankenstein |
| 6,623,983 B1 | 9/2003 | Terstappen et al. |
| 6,660,159 B1 | 12/2003 | Terstappen et al. |
| 6,686,208 B2 | 2/2004 | Meusel et al. |
| 6,727,451 B1 | 4/2004 | Fuhr et al. |
| 6,736,978 B1 | 5/2004 | Porter et al. |
| 6,828,098 B2 | 12/2004 | Langmore et al. |
| 6,833,542 B2 | 12/2004 | Wang et al. |
| 6,858,439 B1 | 2/2005 | Xu et al. |
| 6,872,526 B2 | 3/2005 | Short et al. |
| 7,138,269 B2 | 11/2006 | Blankenstein |
| 7,311,476 B2 | 12/2007 | Gilbert et al. |
| 7,371,051 B2 | 5/2008 | Bau |
| 7,402,131 B2 | 7/2008 | Mueth et al. |
| 7,736,891 B2 | 6/2010 | Nelson et al. |
| 7,749,445 B2 | 7/2010 | Masters |
| 7,807,454 B2 * | 10/2010 | Oh et al. ............ 435/308.1 |
| 8,071,054 B2 * | 12/2011 | Oh et al. ............ 422/527 |
| 2002/0036141 A1 | 3/2002 | Gascoyne et al. |
| 2002/0166760 A1 | 11/2002 | Prentiss et al. |
| 2003/0044832 A1 | 3/2003 | Blankenstein |
| 2003/0080442 A1 | 5/2003 | Unger |
| 2003/0092172 A1 | 5/2003 | Oh et al. |
| 2003/0159999 A1 | 8/2003 | Oakey et al. |
| 2003/0175980 A1 | 9/2003 | Hayenga et al. |
| 2004/0002169 A1 | 1/2004 | Kraus et al. |
| 2004/0009614 A1 | 1/2004 | Ahn |
| 2004/0018611 A1 | 1/2004 | Ward et al. |
| 2004/0121413 A1 | 6/2004 | Aebersoid et al. |
| 2004/0156725 A1 | 8/2004 | Bau |
| 2004/0166577 A1 | 8/2004 | Storek et al. |
| 2004/0224380 A1 | 11/2004 | Chou |
| 2005/0003464 A1 | 1/2005 | Tibbe et al. |
| 2005/0019898 A1 | 1/2005 | Adey et al. |
| 2005/0079591 A1 | 4/2005 | Reich et al. |
| 2005/0121604 A1 | 6/2005 | Mueth et al. |
| 2005/0164181 A1 | 7/2005 | Bricson |
| 2005/0266394 A1 | 12/2005 | Hatton et al. |
| 2005/0266433 A1 | 12/2005 | Kapur et al. |
| 2005/0274650 A1 | 12/2005 | Frazier et al. |
| 2006/0020371 A1 | 1/2006 | Ham et al. |
| 2006/0115971 A1 | 6/2006 | Bau et al. |
| 2006/0177815 A1 | 8/2006 | Soh et al. |
| 2006/0257847 A1 | 11/2006 | Scholtens et al. |
| 2007/0026381 A1 | 2/2007 | Huang et al. |
| 2007/0117158 A1 | 5/2007 | Coumans et al. |
| 2008/0124779 A1 | 5/2008 | Oh et al. |
| 2008/0160634 A1 | 7/2008 | Su et al. |
| 2008/0302732 A1 | 12/2008 | Soh et al. |
| 2009/0047297 A1 | 2/2009 | Kim et al. |
| 2009/0053799 A1 * | 2/2009 | Chang-Yen et al. ....... 435/287.2 |
| 2009/0194420 A1 | 8/2009 | Mariella, Jr. et al. |
| 2009/0201504 A1 | 8/2009 | Ho et al. |
| 2009/0212768 A1 * | 8/2009 | Llandro et al. ........ 324/228 |
| 2009/0220932 A1 | 9/2009 | Ingber et al. |
| 2010/0044232 A1 | 2/2010 | Lin et al. |
| 2010/0090677 A1 | 4/2010 | Britton et al. |
| 2010/0151454 A1 | 6/2010 | Sundararajan et al. |
| 2010/0233693 A1 | 9/2010 | Kopf-Sill et al. |
| 2011/0014600 A1 | 1/2011 | Oh et al. |
| 2011/0127222 A1 | 6/2011 | Chang-Yen et al. |
| 2011/0137018 A1 | 6/2011 | Chang-Yen et al. |
| 2011/0207207 A1 | 8/2011 | Gibson et al. |
| 2012/0108470 A1 | 5/2012 | Oh et al. |

FOREIGN PATENT DOCUMENTS

| | | |
|---|---|---|
| EP | 0364217 | 4/1990 |
| EP | 577643 | 9/1997 |
| EP | 593480 | 11/1997 |
| EP | 920627 | 11/1997 |
| EP | 1356420 | 11/2002 |
| EP | 2271919 | 1/2011 |
| WO | WO 91/02083 | 2/1991 |
| WO | WO 92/04961 | 4/1992 |
| WO | WO 92/16844 | 10/1992 |
| WO | WO 94/11078 | 5/1994 |
| WO | WO 94/15696 | 7/1994 |
| WO | WO 96/27132 | 9/1996 |
| WO | WO 97/07243 | 2/1997 |
| WO | WO 97/46882 | 12/1997 |
| WO | WO 98/10267 | 3/1998 |
| WO | WO 99/49319 | 9/1999 |
| WO | WO 00/32293 | 8/2000 |
| WO | WO 01/51668 | 7/2001 |
| WO | WO 01/96857 | 12/2001 |
| WO | WO 02/054339 | 7/2002 |
| WO | WO 03/046507 | 6/2003 |
| WO | WO 03/066191 | 8/2003 |
| WO | WO 2005/061075 | 7/2005 |
| WO | WO 2006/021410 | 3/2006 |
| WO | WO 2006/122310 | 11/2006 |
| WO | WO 2006/122311 | 11/2006 |
| WO | WO 2006/122312 | 11/2006 |
| WO | WO 2007/044642 | 4/2007 |
| WO | WO 2007/053245 | 5/2007 |
| WO | WO 2007/092713 | 8/2007 |
| WO | WO 2008/048616 | 4/2008 |
| WO | WO 2008/076395 | 6/2008 |
| WO | WO 2009/117611 | 9/2009 |
| WO | WO 2009/129415 | 10/2009 |
| WO | WO 2010/144745 | 12/2010 |

OTHER PUBLICATIONS

International Search Report and Written Opinion, dated Jan. 24, 2011, issued in PCT Application No. PCT/US2010/038229.

US Office Action dated Feb. 1, 2011 issued in U.S. Appl. No. 12/197,169.

US Final Office Action dated Jul. 15, 2011 issued in U.S. Appl. No. 12/197,169.

Bessette, et al., "Rapid Isolation of High-Affinity Protein Binding Peptides Using Bacterial Display", Protein Engineering Design and Selection 2004 17(10):731-739.

Herr, et al., "Integrated Microfluidic Platform for Oral Diagnostics", Annals of the New York Academy of Sciences, 2007, 1098, pp. 362-374.

Hu, et al., "Marker-Specific Sorting of Rare Cells Using Dielectrophoresis", PNAS, 2005, vol. 102, No. 44, pp. 15727-15761.

Inglisa, "Continuous Microfluidic Immunomagnetic Cell Separation", Appl. Phys. Lett., 2004, vol. 85, No. 21, pp. 5093-5095.

Kim, et al., "Simultaneous Sorting of Multiple Bacterial Targets Using Integrated Dielectrophoretic-Magnetic Activated Cell Sorter" Lab on a Chip (2009).

Liu, et al., "Controlling the Selection Stringency of Phage Display Using a Microfluidic Lab on a Chip" (2009).

Lou, et al., "Micromagnetic Selection of Aptamers in Microfluidic Channels," Proceedings of the National Academy of Sciences, USA, 106 (9) 2989-2994 (2009).

Maheswaran, et al., "Detection of Mutations in EGFR in Circulating Lung-Cancer Cells", N Engl J Med, 359:366-77, 2008).

Mauk, et al., "Lab-on-a-Chip Technologies for Oral-Based Cancer Screening and Diagnostics", Annals of the New York Academy of Sciences, 2007, 1098, pp. 467-475.

Miltenyi, et al., "High Gradient Magnetic Cell Separation with MACS", Cytometry, vol. 11 Issue 2, pp. 231-238, 1990.

Nagrath, et al., "Isolation of Rare Circulating Tumour Cells in Cancer Patients by Microchip Technology", Nature, vol. 450: 20/27, 1235-1240, 2007.

Pamme, et al., "On-Chip Free-Flow Magnetophoresis: Continuous Flow Separation of Magnetic Particles and Agglomerates", Analytical Chemistry, 2004, vol. 76, pp. 7250-7256.

Pantel, et al., "Detection, Clinical Relevance and Specific Biological Properties of Disseminating Tumour Cells", Nature Reviews, vol. 8: 329-40, 2008.

Qian, et al., "Rapid Generation of Highly Specific Aptamers via Micromagnetic Selection" Analytical Chemistry (2009).

Radisic, et al., "Micro- and Nanotechnology in Cell Separation", Int. J. Nanomedicine 2006;1:3-14.

International Search Report and Written Opinion dated Dec. 12, 2008, from PCT Appl. No. PCT/US2008/074107.
International Search Report and Written Opinion dated May 12, 2009, from PCT Appl. No. PCT/US2009/037714.
International Search Report and Written Opinion dated Jun. 3, 2009, from PCT Appl. No. PCT/US2009/040866.
US Non-Final Office Action dated Apr. 1, 2010, from U.S. Appl. No. 11/583,989.
US Notice of Allowance dated Aug. 9, 2010, from U.S. Appl. No. 11/583,989.
US Non-Final Office Action dated Aug. 24, 2010, from U.S. Appl. No. 12/197,169.
U.S. Appl. No. 61/037,994, filed Mar. 19, 2008.
U.S. Appl. No. 61/124,565, filed Apr. 16, 2008.
U.S. Appl. No. 61/185,919, filed Jun. 10, 2009.
U.S. Appl. No. 61/313,625, filed Mar. 12, 2010.
U.S. Appl. No. 60/764,390, filed Feb. 2, 2006.
U.S. Appl. No. 60/724,117, filed Oct. 6, 2005.
US Non-Final Office Action dated Nov. 9, 2010, from U.S. Appl. No. 12/871,788.
US Final Office Action dated Apr. 11, 2011, from U.S. Appl. No. 12/871,788.
US Notice of Allowance dated Jul. 29, 2011, from U.S. Appl. No. 12/871,788.
Chinese Office Action dated Feb. 29, 2012, issued in Application No. 200880112841.4.
EP Examination Report dated Jul. 21, 2011 issued in EP07 852801.5.
UK Examination Report, dated Aug. 18, 2011, issued in GB1002776.1.
UK Examination Report, dated Feb. 24, 2012, issued in GB1002776.1.
International Search Report and Written Opinion dated Apr. 16, 2008, from PCT Appl. No. PCT/US2007/022105.
International Preliminary Report on Patentability dated Apr. 22, 2009, from PCT Appl. No. PCT/US2007/022105.
International Preliminary Report on Patentability dated Feb. 24, 2010, from PCT Appl. No. PCT/US2008/074107.
International Preliminary Report on Patentability dated Sep. 21, 2010, from PCT Appl. No. PCT/US2009/037714.
International Preliminary Report on Patentability dated Oct. 19, 2010, from PCT Appl. No. PCT/US2009/040866.
International Preliminary Report on Patentability dated Dec. 12, 2011, from PCT Appl. No. PCT/US2010/038229.
Xia et al., "Combined Microfluidic-Micromagnetic Separation of living cells in Continuous Flow" Biomed Microdevices, 2006, 8(4):299-308.

* cited by examiner

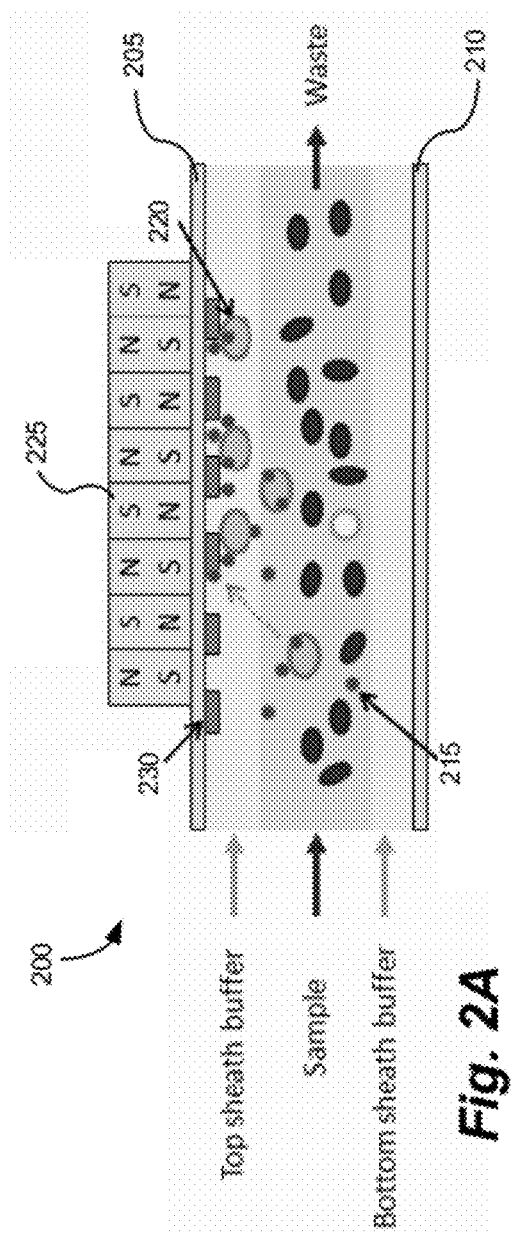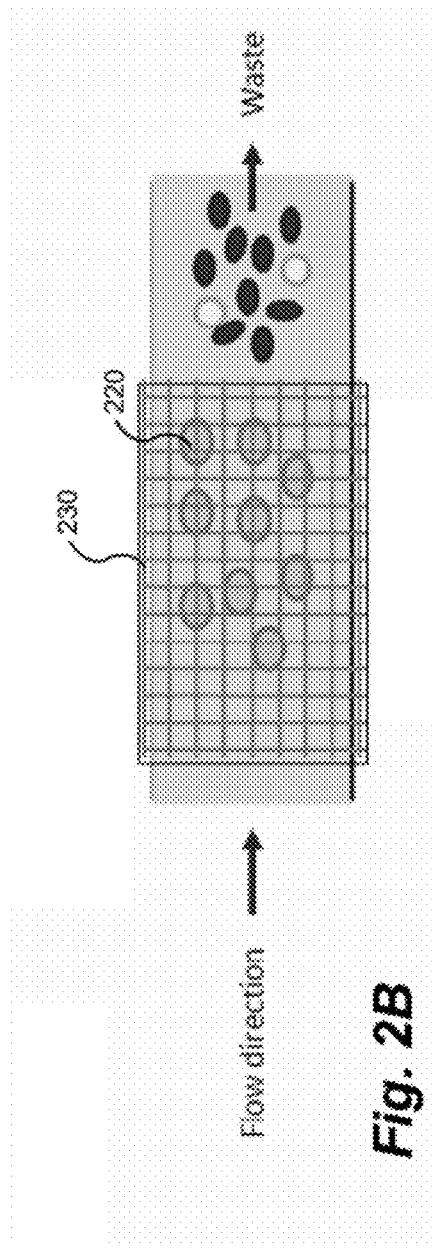
Fig. 2A
Fig. 2B

SHEATH FLOW DEVICES AND METHODS

CROSS-REFERENCE TO RELATED APPLICATIONS

This application claims the benefit of and priority to U.S. Provisional Application No. 61/185,919 filed Jun. 10, 2009, and U.S. Provisional Application No. 61/313,625 filed Mar. 12, 2010, the contents of which are incorporated by reference herein in their entireties.

FIELD OF THE INVENTION

The invention relates generally to fluid processing and, in particular aspects, processing fluids for detection, selection or sorting of particulate moieties. In other aspects the present invention relates to biological fluid processing, detection, sorting or selection of cells, proteins, and nucleic acids. Other aspects are disclosed herein.

BACKGROUND

Particle sorting technologies are widely used for targeting moieties in suspension, but undue contamination can be a technical hurdle to overcome. For example, one may seek to sort relatively rare cells from a complex whole blood sample. Contamination by other cell types may require the need for pre-treatment to enrich for target cells, or post-treatment to remove unwanted non-target cells.

Moreover, contaminating moieties may localize to container sidewalls or other surfaces. Although one may minimize non-specific binding with surface coatings, such as silicone-based products, this may be insufficient. Where there is a horizontal fluid flow plane, and the particles flow in suspension along that plane, they may sink to the bottom (depending on density, viscosity, and other characteristics). Particles may then form a barrier, clogging up the flow path. Plus, contaminating particles may be co-localized in (for example) microfluidic devices configured with a trapping structure. Particularly where target particles are extremely rare, non-specific binding can confound sorting or detection of the target species.

There are ways to enhance particle sorting specificity. In a microfluidic volume, hydrodynamic focusing may be used to transport target moieties. Conventional approaches to hydrodynamic focusing involve using two outer fluidic flows on each side of a central sample flow to laterally constrain the sample flow. See generally, P. Crosland-Taylor, "A device for counting small particles suspended in fluid through a tube," Nature 171:37-38 (1953) doi: 10.1038/171037b0 for a seminal paper on the subject of flow cytometry, and the use of fluidic sheaths.

In general, sheath flow is a particular type of laminar flow. Although sheath flow may be configured as an outer flow "tube" surrounding a fluid stream, or other fluidic path for total or partial surrounding of a fluid stream, sheath flow herein also includes a fluidic flow path in laminar flow with respect to an adjacent, parallel fluid flow path. Thus, what is a laminar flow plane on a solid surface is considered a sheath flow plane when on a fluid "surface" (e.g., the adjacent, parallel fluid flow path). Sheath flow implies substantially no turbulent flow, as undue turbulence would result in intermixing of fluidic flow paths (and the fluidic laminar flow plane layer would no longer function as a "sheath"). As such, laminar flow, rather than turbulent flow, is necessary to create sheath flow.

Depending on the architecture and fluid characteristics, sheath flow may function to hydrodynamically focus a fluid sample (by surrounding a sample flow path without intermixing), or, where there is a layer (or sheath incompletely surrounding a fluid flow), the fluid in a laminar flow plane may act as a fluidic extension of a device wall—essentially acting as a fluidic barrier between a fluidic sample and surrounding solid surfaces.

Sheath flow is particularly useful in a microfluidic context, where particles in suspension may disrupt or block microfluidic circuitry. Thus, hydrodynamic focusing or sheath flow allows for faster sample flow velocity, and higher throughput.

Nevertheless, creating laminar sheath flow useful for microfluidic devices (or larger devices) is problematic. Conventional devices, such as conventional flow cytometers require complex instrumentation with specialized components, and fabrication is particularly detailed. Although there may be particular geometries and architectures reportedly creating microfluidic sheath flow, there exists a need for easy to manufacture, predictable sheath flow devices useful at the macro- and micro-fluidic scales, particularly for improved sensitivity in target moiety sorting, and reducing non-specific binding to surfaces.

SUMMARY

The present invention provides sheath flow based devices, manufacturing and instrumentation systems, methods of use, methods of manufacture, and related aspects.

The present invention stems from the observation that sheath flow may be obtained downstream of a laminar flow established on a solid surface. Where the solid surface is discontinued, the laminar flow essentially continues as established, except, where configured such that the flow plane abuts a fluid stream in an adjacent, parallel fluid flow plane, it functions as "sheath flow." This observation gave rise to a number of aspects and applications of the present invention. Thus, sheath flow, advantageous in many fluidics applications, is easily established without the need for complex instrumentation.

In particular aspects, the present invention relates processing biological fluids and particles, including, but not limited to blood and fractions thereof, cells, nucleic acids and proteins, and other analytes found in or relating to biological functions. Other aspects will be apparent one of ordinary skill in the art in view of the present disclosure.

BRIEF DESCRIPTION OF THE DRAWINGS

FIGS. 2A and 2B are illustrations presenting a cross-sectional side view and a top view, respectively, of a device configured for magnetophoretic particle separation.

DETAILED DESCRIPTION

As noted above, the present invention stems from the observation that once a laminar flow path is established on a solid surface, it can continue as a sheath flow abutting an adjacent, parallel laminar flow path plane. Thus, even without the solid surface used to originally establish laminar flow, the fluid will continue in the flow path and flow plane as established when adjacent to one or more parallel fluid laminar flow planes. In some embodiments, a laminar sample flow path is established adjacent to one or two buffer flow paths. In this way, a sheath flow is established, whereby the sample flow path is prevented from contacting interior surfaces of a sheath flow device.

Figure 1:
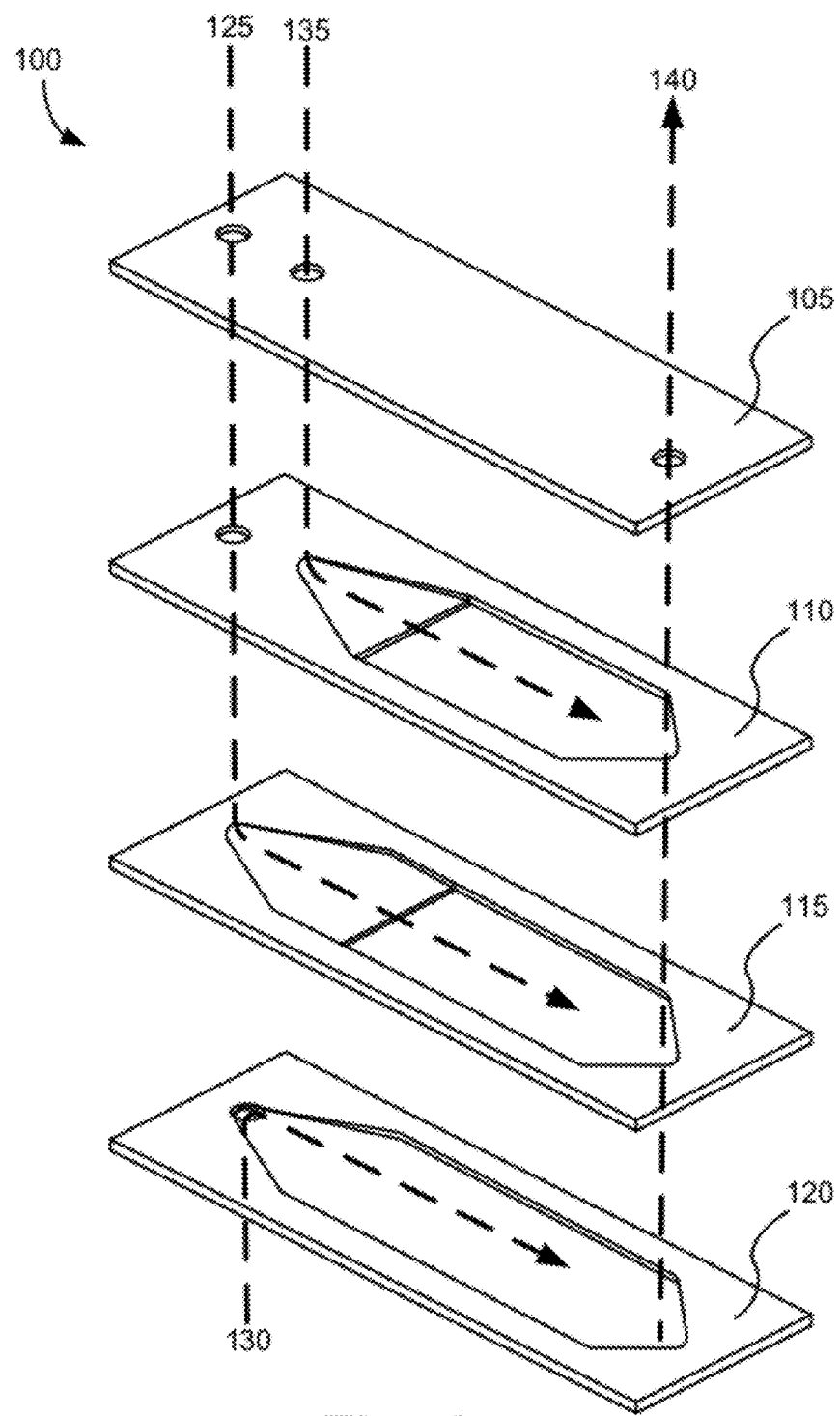
FIG. 1 is a schematic illustration of a sheath flow device where four component plates are used to establish a laminar buffer flow above and below a sample laminar flow.

FIG. 1 depicts an exploded perspective of a sheath flow device, 100, of the invention. Sheath flow device 100 includes four parallel plates, 105, 110, 115 and 120, that, when adjoined, form sheath flow device 100. A sample fluid is introduced via an access port in plate 105, in the "z" axis, as indicated by dashed arrow 125. The fluid sample strikes, for example, a milled surface on plate 115 and is deflected and, by virtue of the chambering, the sample fluid is directed along the solid surface thereby establishing a laminar flow path. The solid surface is discontinued (e.g. as the fluid passes the end of the solid surface or otherwise discontinues contact with the solid surface) in the laminar flow path plane, and the fluid continues as a laminar flow. Buffer fluid is introduced via inlets in plates 120 and 105, as indicated by dashed arrows 130 and 135. Each of the buffer streams strikes a similar surface, on plates 115 and 110, respectively, an also establish laminar flows adjacent to the sample laminar flow. These laminar flows continue as separate layers of laminar flow, thereby creating a sheath flow. That is, the sample laminar flow is sheathed by the buffer laminar flows, for example, preventing the sample flow from touching certain interior surfaces of the sheath flow device.

Thus, the present invention, in one aspect, provides a sheath flow device including: (a) a first laminar flow establishing solid surface upstream of a sheath flow plane area; (b) a sample laminar flow area in parallel with the sheath flow plane area; and optionally, (c) a second laminar flow establishing solid surface upstream of a second sheath flow plane area.

As with the configuration illustrated in FIG. 1, one may establish sheath flow using a device of the present invention configured to establish one or more parallel laminar flow planes on corresponding solid surfaces upstream of corresponding sheath flow planes. Embodiments described herein include sheath flow devices with magnetic separation stations, which deflect and optionally trap magnetically labeled sample components. Exemplary magnetic trapping stations are described in, e.g., US Patent Publication 20090053799A1, "Trapping Magnetic Sorting System for Target Species," herein incorporated by reference for all purposes. In certain embodiments, the sheath flow devices employ non-magnetic forces to drive separation. Examples of these forces include acoustic forces, optical forces, and dielectric forces.

FIGS. 2A and 2B are illustrations presenting a cross-sectional side view and a top view, respectively, of a sheath flow device, 200, of the present invention configured for magnetophoretic particle separation. Device 200 includes a top plate, 205, and a bottom plate, 210. A complex sample containing a target moiety (e.g., cells 220 as illustrated) is in a laminar flow layer between a top fluidic layer and a bottom fluidic layer. A structure for particle selection, here, a nickel ferromagnetic structure, 230, is located on the inside surface of top plate 205, such that the sample in laminar flow is prevented from direct contact by the top buffer sheath flow. In one embodiment, the nickel structure is isolated, for example coated with a material, so that the collected targets species, such as live cells, do not directly contact the (potentially toxic) nickel. External controllable force (here, magnetic) is applied to magnetophoretically sort selective particles (as illustrated, cells selectively labeled with magnetic particles 215, and thereby be responsive to magnetic selection). FIG. 2B illustrates a top-down view, showing that waste is not deflected or trapped by the magnetophoretic structure, and passes in the sample fluid flow. Further aspects of this embodiment are described below.

Figure 2C:
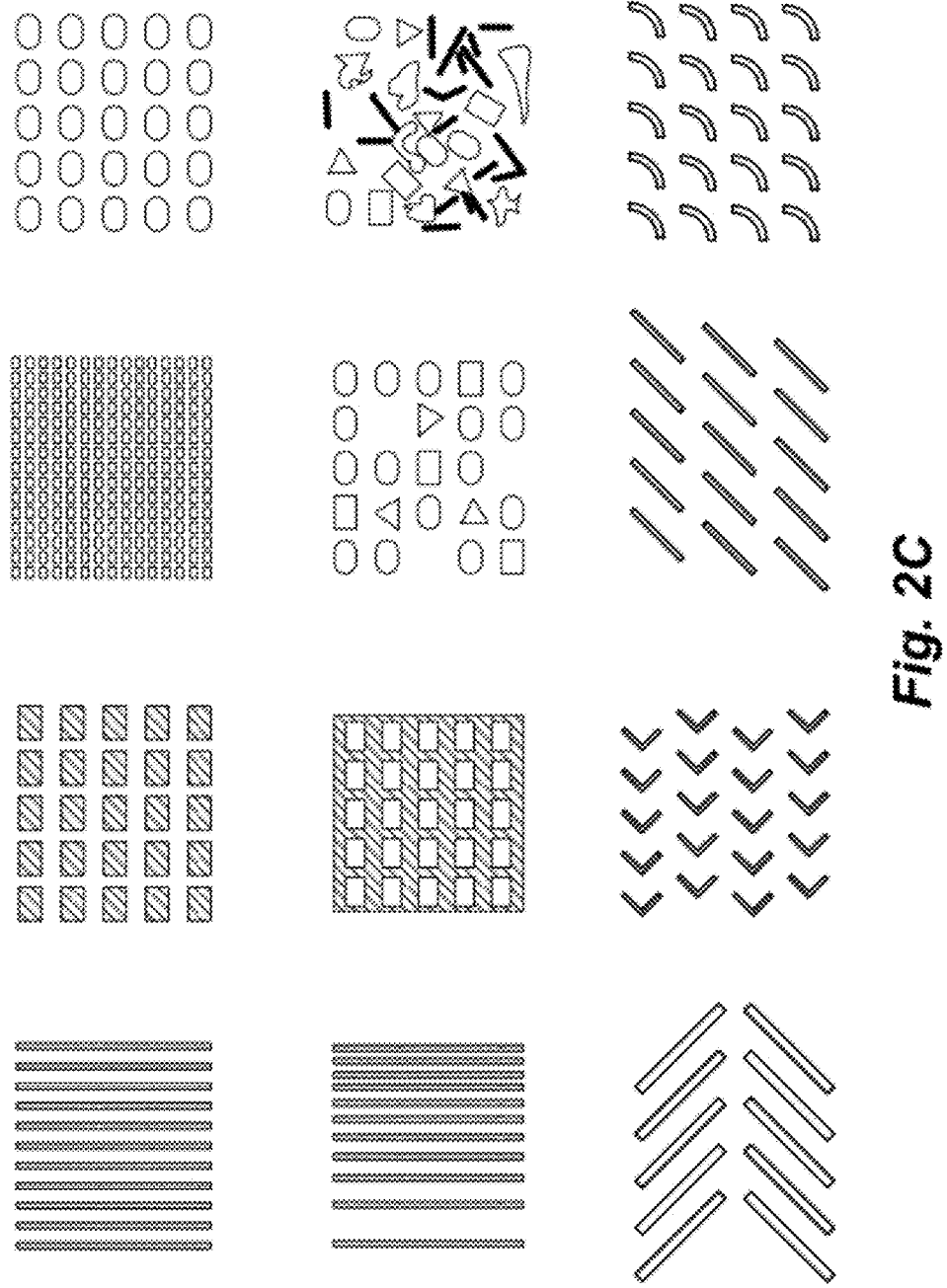
FIG. 2C shows various structures of magnetic traps suitable for sheath flow devices described herein.

FIG. 2C shows nine variations of magnetic trapping grids or patterns that can be used in sheath flow devices described herein. These serve as a magnetic field gradient generating (MFG) structures. In one embodiment, the magnetic trapping grids or patterns are made of magnetic materials. In another embodiment, the magnetic trapping grids or patterns are formed, for example micromachined or screen printed, from materials which are used in conjunction with external magnets that induce a highly localized strong magnetic field in the magnetic trapping grid or pattern in order to pull the magnetic-particle-labeled target species from the sample flow, through the buffer sheath flow and onto the magnetic trapping grid or pattern.

In general, devices and related methods and systems of the present invention establish discrete fluidic laminar flow layers that are substantially free or essentially free of turbulent flow, such that the fluidic layers remain discrete. As used herein with reference to the laminar sheath flow, the term "substantially free of turbulent flow" with reference to laminar sheath flow denotes that there may be some turbulent flow, although the sheath flow result is still achieved. The term "essentially free" as used in this context denotes that there may be some unavoidable turbulent flow, but, as indicated above, the desired laminar sheath flow layers are achieved.

Sheath flow, in some aspects, provides a fluidic barrier between a sample fluid (from which one seeks a separation or detection of a target moiety) and a solid surface, thereby functioning as an isolation barrier to solid surfaces. For example, sheath flow is used to reduce non-specific binding of any non-target moieties to the solid surfaces. The present invention thus provides means to prevent unwanted interaction of a sample fluid's components with solid surfaces of the device. Desirable interactions, for example selective collection of fluid components, is achieved with undesirable interactions between the sample fluid and solid surfaces. For example, devices of the invention can be used to prevent undue non-specific binding of non-target moieties within a sample fluid laminar flow plane, by providing a sheath flow barrier substantially preventing sample fluid contact with solid surfaces—like sidewalls, or top or bottom solid surfaces, trapping stations (as described above) and the like.

Additionally, sheath flow may be employed to "pinch" or otherwise laterally narrow the flow of sample to thereby provide a narrow flow of sample that can be used for purposes such as counting cells in the sample. In certain embodiments, the laminar sheath flow bounds a laminar sample flow having a width comparable in dimension to that of the cells or other target species being detected. Other aspects will be apparent to one of ordinary skill in the art in view of the present disclosure.

Terminology:

Unless otherwise defined, scientific and technical terms used in connection with the present invention shall have the meanings that are commonly understood by one of ordinary skill in the art.

General terminology: In this application, the use of the singular includes the plural unless specifically stated otherwise. In this application, the word "a" or "an" means "at least one" unless specifically stated otherwise. The phrase "at least one of" followed by a list means any one or more members of the list and does not mean that all listed members must be present. The use of "or" means "and/or" unless specifically stated otherwise. In the context of a multiple dependent claim, the use of "or" refers back to more than one preceding independent or dependent claim in the alternative only. Furthermore, the use of the term "comprising," as well as other forms, such as "comprises" and "comprised," is not limiting. Also, terms such as "element" or "component" encompass both elements and components including one unit and elements or components that include more than one unit unless specifically stated otherwise. Where a "skilled practitioner" is referenced, this refers to an ordinary skilled practitioner in the art to which the subject matter pertains, in context, unless otherwise noted.

Fluid mechanics/fluid dynamics terminology: The various terms describing fluid mechanics (including microfluidics), are used in their conventional technical meanings.

The term "fluid" and the term "liquid" are used synonymously herein to refer to substances that flow and optionally take the shape of a container. Under some circumstances, there may be gaseous or solid substances that flow. For example, finely granular materials may flow.

The term, "fluidic circuit" refers to a configuration of fluidically interconnected functional areas located in the present sheath flow devices. As described in more detail herein, functional areas include reservoirs or compartments and channels through which fluids may flow. The channels may be optional, for example, where two compartments are directly fluidically connected as by an adjoining wall. Two reservoirs or chambers may be reversibly fluidically connected, such as via adjoining wall that may be sealed and opened, or may be porous, allowing only certain size particles to flow through. A skilled practitioner will appreciate the numerous configurations possible for the present fluidic circuitry. Apart from configuration, there are similarly wide varieties of choices to integrate fluidic circuits, such as the flow control structural elements described herein.

Particle sorting terminology: The term "moiety" as used from time to time herein denotes a "portion" and includes reference to a particle. A "particle" refers to a small object that behaves as a whole unit in terms of its transport and properties. The term "analyte" can be a "moiety" or a "particle" and is used in its ordinary meaning as a substance the presence of which is detected, or a characteristic of which is measured, in an analytical procedure.

Biological and biochemical terminology: Where specific categories of molecules are discussed, such as nucleic acids or proteins, synthetic forms are included, such as mimetic or isomeric forms of naturally occurring molecules. Unless otherwise indicated, modified versions are similarly encompassed, so long as the desired functional property is maintained. For example, an aptamer selective for a CD34 cell surface protein includes chemical derivatives (e.g., pegylated, creation of a pro-form, derivatized with additional active moieties, such as enzymes, ribozymes, etc.)

The term "biological fluid" denotes the source of the fluid, and includes (but is not limited to) amniotic fluid, aqueous humor, blood and blood plasma (and herein blood refers to the plasma component, unless otherwise expressly stated or indicated in context), cerumen (ear wax), Cowper's fluid, chime, interstitial fluid, lymph fluids, mammalian milk, mucus, pleural fluid, pus, saliva, sebum, semen, serum, sweat tears, urine, vaginal secretion, vomit and exudates (from wounds or lesions).

The term "selective binding molecule" denotes a molecule that selectively, but not necessarily specifically, binds to a particular target moiety. The binding is not random. Selective binding molecules may be selected from among various antibodies or permutations (poly- or monoclonal, peptibodies, humanized, foreshortened, mimetics, and others available in the art), aptamers (which may be DNA, RNA, or various protein forms, and may be further modified with additional functional moieties, such as enzymatic or colorimetric moieties), or may be particular to a particular biological system. Proteins may be expressed with particular "tags" such as a "His-tag", and a skilled practitioner will determine appropriate kinds of selective binding molecules or detectable labels are suitable. The list is not exhaustive.

It should be understood that embodiments of the invention are not limited to biological or even organic samples, but extend to non-biological and inorganic materials. Thus, the apparatus and methods described herein can be used to screen, analyze, modify, or otherwise process a wide range of biological and non-biological substances in liquids. The target and/or non-target species may include small or large chemical entities of natural or synthetic origin such as chemical compounds, supermolecular assemblies, proteins, organelles, fragments, glasses, ceramics, etc. In certain embodiments, they are monomers, oligomers, and/or polymers having any degree of branching. They may be expressed on a cell or virus or they may be independent entities. They may also be complete cells or viruses themselves.

General Considerations:

General considerations for making and using the present invention include the overall device configuration, materials, manufacturing systems, instrumentation systems, and applications. Particular embodiments including working examples are also presented. Prophetic examples are also included below.

In making or using the present invention, one will generally consider fluid dynamics principles including: compressible versus incompressible flow, viscous versus inviscid flow, steady versus unsteady flow, laminar versus turbulent flow, Newtonian versus non-Newtonian fluids, subsonic versus transonic, supersonic and hypersonic flows, non-relativistic versus relativistic flows, magnetohydrodynamics (or other considerations of particle sorting). The list is incomplete, but a practitioner will recognize that fluid, particle, device and sorting methods must all integrate.

Thus, among other things, the present invention may be used for selecting rare cells, such as circulating tumor cells, from a blood sample, while minimizing non-selective binding that could confound results. For particles of cellular dimensions, physical constraints imply that the hydrodynamically focused stream requires a velocity of several meters per second. At this speed a typical cell would traverse its own diameter in a few microseconds.

The present devices may be configured for additional functions. For instance, one may seek to first isolate cells, and then culture the cells in situ; thus the present devices may be additionally configured for use as a bioreactor. Moreover, one may first culture cells, or use pre-grown cells, to obtain protein (or other target moiety) on the present sheath flow device. The target protein (or moiety) may then be detectably labeled and suspended in fluid, to be sorted in the present sheath flow device. The present invention may be used for sorting or screening libraries of chemicals, i.e., by selecting for protein to which an aptamer from an aptamer library.

The present sheath flow device may be used in any way that current fluid handling devices are used. General considerations include the desired manufacturing method systems, the desired use, and the desired related instrumentation (if any). One will consider device geometries in conjunction with sample size and application requirements, means for controlling fluid flow direction, path, and rate; means for selecting or sorting particulate matter (if desired), as well as adaptation with instrumentation required.

The present sheath flow devices, related methods and systems, have industrial application in both macro-fluidic as well as microfluidic samples, and, as more fully described below, may be configured and adapted for a wide variety of purposes. Microfluidic devices are available for such purposes as on-protein purification, rare cell separation, and screening for rare molecules (such as proteins or aptamers) in a sample. These may be configured with the present laminar flow establishing surface, to establish sheath flow in fluidic layers as described herein. See, e.g., J. Qian, X. Lou, Y. Zhang, Y. Xiao, H. T. Soh, "Rapid Generation of Highly Specific Aptamers via Micromagnetic Selection" *Analytical Chemistry* (2009); U. Kim and H. T. Soh, "Simultaneous Sorting of Multiple Bacterial Targets Using Integrated Dielectrophoretic-Magnetic Activated Cell Sorter" *Lab on a Chip* (2009); Y. Liu, J. D. Adams, K. Turner, F. V. Cochran, S. Gambhir, and H. T. Soh, Controlling the Selection Stringency of Phage Display Using a Microfluidic. *Lab on a Chip* (2009); X. Lou, J. Qian, Y. Xiao, L. Viel, A. E. Gerdon, E. T. Lagally, P. Atzberger, T. M. Tarasow, A. J. Heeger, and H. T. Soh, "Micromagnetic Selection of Aptamers in Microfluidic Channels," *Proceedings of the National Academy of Sciences, USA,* 106 (9) 2989-2994 (2009), all of which are herein incorporated by reference.

General Configuration of Sheath Flow Devices:

The present sheath flow devices will be configured in accordance with the principle of establishing a laminar flow on a solid surface that continues as sheath flow once the fluid layer comes in contact with another fluid layer (such as upon discontinuation of contact with the solid surface, as described herein). The present sheath flow devices can have any number of configurations and architectures so long as a solid surface is available to establish a laminar flow upstream of fluidic contact with an adjacent fluid in a parallel laminar flow path plane.

Generally, the present invention provides devices configured for sheath flow acting as a barrier between a fluid sample flow path and a device surface. This barrier inhibits or prevents interaction of the sample fluid with device surfaces. In one example, this barrier substantially prevents non-specific binding of moieties in the subject fluid sample to the solid surface. By substantially preventing non-specific binding, deleterious effects, such as disruption of path flow by accumulation of moieties, or contamination of selected rare moieties, can be avoided.

Spatially, where a sheath flow device is positioned horizontally (with respect to a horizon), the flow paths are vertically aligned (e.g., layered one atop the other) with respect to each other. This is illustrated in FIGS. 1 and 6A-C, where the top sheath and the bottom sheath flows are parallel with and adjacent to either side of the sample flow plane. The top sheath is on "top", the bottom sheath is on the "bottom" and therefore stacked in a vertical orientation, although the flow plane is horizontal.

One may similarly configure the present devices in a vertical orientation (perpendicular to a horizon). With respect to a vertical orientation, the flow paths are layered horizontally, (e.g., left to right with respect to each other).

Depending on the fluid circuitry, the flow paths may or may not be in a flat plane. Where the flow paths are configured in the shape of a semi-circular channel, circular tube, or similar channeled configuration, the flow paths will be substantially parallel (non-intersecting, in accordance with Euclidian geometry for a curved planar three dimensional shape).

In some circumstances, one may have a substantially stationary fluid "pool" acting as a fluid sheath. Although strictly speaking a pool of fluid is not flowing, particularly viscous liquids (e.g., substances taking the shape of a container in which they are in) may display fluid movement characteristics but extremely slowly. As such, one may configure a device of the present invention to have such a "pool" area, such as a bottom fluid layer (see below) upon which a less viscous fluid sample flows.

Size: The present device can be scaled to any size, with particular consideration of fluid mechanic/dynamics, and fluid characteristics. In one embodiment, the devices of the invention are scaled for microfluidic circuitry. In other embodiments, devices of the invention are configured for liter or multi-liter scale use.

With respect to the laminar flow establishing area, considerations include the surface area necessary to establish a laminar flow in view of the fluid characteristics.

As one of ordinary skill in the art would appreciate, fluid characteristics include viscosity, particulate matter characteristics (such as hydrodynamics), particulate matter concentration, and the degree to which the fluid is miscible (or otherwise reacts with) fluid in an adjoining layer, for example.

With regard to size, the amount of pressure for a desired amount/rate of flow may be calculable based on fluid dynamics considerations, including: compressible versus incompressible flow, viscous versus inviscid flow, steady versus unsteady flow, laminar versus turbulent flow, Newtonian versus non-Newtonian fluids, subsonic versus transonic, supersonic and hypersonic flows, non-relativistic versus relativistic flows, magnetohydrodynamics, and other approximations according to methods known in the art. One of ordinary skill in the art would consider fluid dynamics in view of the overall system, including the device materials.

The sheath flow device will have a direction over which a separation force acts to deflect target species from a sample flow plane into a sheath flow plane. Generally, this direction will be perpendicular to the direction of flow and the sheath and sample flows will form parallel adjacent layers, sitting on top of one another along this direction. The device dimensions in this direction (the device's "height") will be relatively small, often the smallest in the device, and on the order of the distance over which the separation force acts. As these forces are often short range forces, the device dimension in this direction often will be on the order of one millimeter or less. In contrast, the transverse device dimension, the dimension in a direction perpendicular to both the direction of flow and the direction of the separation force, can be quite large. This allows the devices to scale to relatively large sizes and allow corresponding increases in throughput, in some cases on the order of hundreds of milliliters per hour in a microfluidic format. In some cases, this transverse device dimension is at least about 10 centimeters or even at least about 20 centimeters. In a specific embodiment, the device's height is about 700 micrometers and its transverse dimension is about 20 centimeters. The dimensions presented here are well suited for use with magnetophoretic separation mechanisms including any of those described elsewhere herein.

Currently, the working examples relate to microfluidic sizes (generally having fluidic channel diameters of 1 mm or less, see the Examples, below). Apart from limitations on practicable application, the lower limit of size is constrained predominantly by manufacturing methods. For example, if one desires nano-electronic components, one may have such components integrated using micro-lithographic techniques. For microfluidic applications, one may seek to proportions limiting turbulence in fluid flow and optimizing laminar flow in a desired path. The present sheath flow devices may be configured for use with sample volumes of 1-10 µL 10-100 µL, 100-1000 µL, 1000 µL-100 ml, for example.

The present sheath flow devices may be scalable to virtually any size, again with practical considerations such as fluid mechanic and fluid dynamics principles and the desired application. The general principle of establishing a laminar flow upstream of a sheath flow is broadly applicable to devices larger than those for microfluidic applications, and one of ordinary skill in the art will recognize the general fluid dynamic principles allowing scale-up. For example, in some embodiments the present devices can be configured for use with larger sample volumes from between about 100 ml to 1 liter, and in some cases multi-liter scale.

Number of and characteristics of fluid layers: The term "fluid layer" is used herein to denote a discrete fluidic flow path plane, substantially free of turbulent flow. The "fluid layer" may be a laminar flow on a solid surface, or, a sheath flow with respect to an adjacent, abutting, fluid layer in a parallel plane.

While not in a two-dimensional planar orientation, the present invention also applies to devices having a total sheath surrounding sample fluid. A combination of these laminar flow establishing surfaces may be used to create fluid layers surrounding a sample, thereby permitting 3D hydrodynamic focusing to be readily achieved. In this way, a sample flow is isolated from a channel wall (in device fluidic circuitry) both horizontally and vertically.

Number of Fluid Layers: In a general aspect, the present invention provides devices (and related methods and systems) including at least three discrete, serially adjoining, fluid laminar flow layers. The laminar flow paths are positioned adjacent to each other, and parallel with each other, in series. Each laminar flow path is parallel with respect to the others, and layered perpendicularly with respect to their flow paths.

Three layers may be used (as in the working example below), such that a sample laminar flow plane is sandwiched between an upper and lower layer (for example). One may add additional fluid layers, although the extent to which a laminar (sheath) flow plane is continued in the absence of solid support will largely depend on fluid mechanic considerations. One may consider the characteristics of the fluidic circuitry, such as the geometric configuration, channel wall composition and frictional force. Other considerations relate to the flow velocity and force, the flow plane dimensions, the fluidic volume in each flow plane layer, and other fluid mechanic considerations appreciated by a skilled practitioner.

Fluid Layer Thickness: Related to the number of fluid layers, the thickness (or depth) of each fluid layer is important. A practitioner will appreciate that device configuration and application, as well as fluid characteristics will determine fluid layer thickness.

For example, where a sheath flow device is configured for magnetophoretic, the magnetic force should be greater than the resistance provided by a fluid layer providing sheath flow. That is, the magnetic force applied to separate magnetically labeled target particles from solution should be sufficient to pull the particles to the desired region (say, a trapping station, see above), through the fluid layer.

Thus, for example, where one seeks a magnetophoretic device having a trapping station on an upper surface, such that the magnetic force is applied to the top of the device in a horizontal plane, the present sheath flow device may include a relatively viscous (with respect to sample viscosity), slow moving (or stationary) first (e.g., bottom) fluid layer, a relatively non-viscous (with respect to the bottom layer) sample layer, and top layer essentially free of viscosity. In that way, the sheath flow of the top layer substantially prevents non specific binding in the magnetic trapping station (located on the top surface), yet doesn't prevent magnetically labeled target particles from traveling through the layer to be trapped.

Structural Elements:

In general, the present sheath flow devices function to provide fluidic movement to effectuate a particular application, beyond simple fluid containment or storage.

Structural features provide for this fluid circuitry. The present sheath flow devices include one or more access ports, one or more reservoirs, and one or more channels providing fluidic communication between or among access ports and reservoirs. Other structural components are also described.

Access ports: In general, depending on the overall configuration and materials, the present sheath flow devices will have at least one access port where materials are admitted or exited, and at least one reservoir for containing a fluid. Access ports, used for fluid (or other material) entry or exit, may be configured to operate with other apparatus or instrumentation as part of an overall system.

Access ports may connect with external environment, such as by providing a way for fluid fill or fluid exit. For fluid fill, the access port may be configured for fill via syringe, pipette, or by automated filling instrumentation. This is illustrated in FIG. 6B, where an access port is fitted with an adapter suitable for a syringe. Fluid exit may be, for example, waste disposal. Or, exit may be part of a positive selection scheme, whereby particulate matter in a suspension is selectively captured. Various types of external interconnects for access ports may be used, such as tubing studs, hose barb connections, O-ring connections, or other external types of interconnections.

Access ports, rather than being an external interconnection, may alternatively be in fluid communication with another portion of the device, such as a separately enclosed reservoir. Functionally, the same purpose is served, e.g., fluid fill or fluid partitioning (exit).

Devices of the present invention can have one or more than one access port for a variety of functions, such as for introducing a number of different fluids or for exiting separate moieties, and each may optionally be connected with the external environment or with another portion of the device.

Reservoirs: The present device also includes at least one reservoir for containing a fluid, and performing any functions on the fluid. Reservoirs may serve a functional purpose, and include additional structural elements to effect such purpose. For example, where cultured cells are desired, one may have suitable cell culture apparatus integrated with the reservoir, such as (but not limited to) aeration devices, mixers, or temperature controls. These devices may form a part of the present sheath flow device, or may be part of related processing instrumentation where their device integration is temporary (when the sheath flow is operably connected to the instrumentation). Reservoirs may be adapted to operate within a system for fulfilling a function.

Device Functional Components: One may configure or adapt the present devices for filling and measuring fixed volumes, or for continuous flow. The present device may be configured for multiplexed functions (such as cell lysis and protein isolation). The present device may be configured for a single or multi-step process or assay, and may be configured for reagent storage. The present device may include filtration configurations or adaptations.

For example, the present sheath flow device may further include a structure for trapping target moieties, as a form of particle sorting, for example. For example, as explained below, one may include a ferromagnetic grid for magnetophoretic particle sorting, to act as a "trapping station" for magnetically bound target species. Separating particles from a suspension may be particularly advantageously performed in the present sheath flow device. For example, where magnetophoretic separation of a particular moiety from a complex mix is desired, one may have suitable magnetophoretic trapping structures in place, such as a ferromagnetic structures as described in US Patent Publication 20090053799A1 cited above. This is illustrated in FIG. 6B, where a ferromagnetic trapping station is included on an upper layer.

A variety of particle sorting/detecting/analytical functionalities may be included, as indicated in this specification, passim.

Examples of operational modules that may be integrated with magnetic trapping sorters in sheath flow fluidics devices include (a) additional enrichment modules such as fluorescence activated cell sorters and washing modules, (b) reaction modules such as sample amplification (e.g., PCR) modules, restriction enzyme reaction modules, nucleic acid sequencing modules, target labeling modules, chromatin immunoprecipitation modules, crosslinking modules, and even cell culture modules, (c) detection modules such as microarrays of nucleic acids, antibodies or other highly specific binding agents, and fluorescent molecular recognition modules, and (d) lysis modules for lysing cells, disrupting viral protein coats, or otherwise releasing components of small living systems. Each of these modules may be provided before or after the magnetic sorter. There may be multiple identical or different types of operational modules integrated with a magnetic sorter in a single fluidics system. Further, one or more magnetic sorters may be arranged in parallel or series with respect to various other operational modules. Some of these operational modules may be designed or configured as traps in which target species in a sample are held stationary or generally constrained in particular volume.

As should be apparent from the above examples of modules, operations that may be performed on target and/or non-target species in modules of integrated fluidics devices include sorting, coupling to magnetic particles (sometimes referred to herein as "labeling"), binding, washing, trapping, amplifying, removing unwanted species, precipitating, cleaving, diluting, ligating, sequencing, synthesis, labeling (e.g., staining cells), cross-linking, culturing, detecting, imaging, quantifying, lysing, etc.

Specific examples of biochemical operations that may be performed in the magnetic sorting modules of integrated fluidic devices include synthesis, purification, and/or screening of plasmids, aptamers, proteins, and peptides; evaluating enzyme activity; and derivatizing proteins and carbohydrates. A broad spectrum of biochemical and electrophysiological assays may also be performed, including: (1) genomic analysis (sequencing, hybridization), PCR and/or other detection and amplification schemes for DNA, and RNA oligomers; (2) gene expression; (3) enzymatic activity assays; (4) receptor binding assays; and (5) ELISA assays. The foregoing assays may be performed in a variety of formats, such as: homogeneous, bead-based, and surface bound formats. Furthermore, devices as described herein may be utilized to perform continuous production of biomolecules using specified enzymes or catalysts, and production and delivery of biomolecules or molecules active in biological systems such as therapeutic agents. Fluidic devices as described herein may also be used to perform combinatorial syntheses of peptides, proteins, and DNA and RNA oligomers.

Integration and Fluidic Circuitry: Integration of functional elements may be accomplished any number of ways. In general, one may fluidically connect access ports and reservoirs in all combinations via flow channels. Flow channels may be adapted for the kind of flow so desired, and may be of any dimensions that permit desired fluidic movement.

Flow control structural elements may be selected from a wide variety. These can be valves, porous membranes, mixers, pumps, and other traditional flow control structural elements. Non-conventional flow controls may be used, such as adaptation of material that solidifies in situ to block flow.

One should consider the laminar flow establishing surface in conjunction with integration of fluidic circuitry. For example, if there is a laminar flow established upstream of a sheath flow, the sheath flow should be non-interfering in a backward-incompatible (upstream) way.

All or part of the present device may be biodegradable, such as using polymeric material that degrades to non-toxic constituent moieties in the presence of heat, sunlight, water, etc.

Inventory considerations further include product identification, such as bar coding, RFID, or other means to identify devices. The present devices may be further packaged with related reagents. For example, for use with biological reagents, one package the present device with suitable buffers, media, detectable labeling moieties, apparatus (such as syringes for fluid fill), or other items.

Wash or Carrier Fluids: The present devices may be configured or adapted for use with, for example, aqueous buffers (with or without detergents), alcohols (methanol, ethanol, isopropanol for example), organic solvents (hexane, fluorocarbons, aromatic for example), or a combination of any of the above. These fluids may, in certain embodiments, serve as the sheath flow fluid.

Electrochemical/electro-active: The present devices may include one or more printed circuit boards, interdigitated electrodes, sputter or screen printed electrodes, or capacitance arrays. For example, one may pre-prepare circuit boards on polymeric material, and use that to manufacture the present sheath flow devices. These elements may be controlled by associated logic which directs operation of trapping stations and/or various pre- and post-processing modules or stations.

Operability with forces used for particle trapping or sorting: One of the most promising applications for the present device is particle sorting, and there are number of ways this can be done. A controllable force, such as magnetic, acoustic, electrophoretic, or optical is used to move a responsive particle suspended in a fluid.

One may, for example, contemplate use of magnetic activated particle sorting (such as cell sorting). Practicably, this involves using magnetic beads to which a selective binding molecule is attached. When the selective binding molecule binds to the desired target, the magnet is thus so attached. The desired target can then be trapped or sorted using magnetic force, and optionally a ferromagnetic trapping station. Thus, one may embed ferromagnetic material in the sheath flow device material, such as a printed magnetic area or by incorporating ferromagnetic dust particles into a manufacturing material (for application in a particular area, for example). One may similarly use other controllable forces as are available in the art such as acoustic, electrophoretic or other forces. A skilled practitioner will appreciate the appropriate device configuration to accommodate the present system.

Optical Detection: The present devices may be configured to permit optical detection. This has practical applicability, for example, if colorimetric, fluorescent, or luminescent detectable markers are desired. Other optical interfaces may include fiber optic, surface plasmon resonance, attenuated total reflection or other optic interfaces.

Other Features/Special requirements: The present devices may be sterilized (such as with ethylene oxide, considering the durability of the selected material to other sterilization techniques, such as autoclavability). There may be surface compatibility with cell culture requirements, and additional surface energy in materials or configurations so selected. The present device may be, for example, gas permeable. One may seek internal coatings, such as silicon, to minimize non-specific binding to a surface.

Magnetophoretic and Magnetic Trapping Embodiments: With the above principles in mind, various designs including both sheath flow and magnetic sorting may be envisaged. In certain embodiments magnetic sorting involves a trapping mode where the non-target and target species are sequentially eluted after the application of the external magnetic field. In other words, the species attached to magnetic particles are held in place while the unattached species are eluted. Then, after this first elution step is completed, the species that are attached magnetic field and were prevented from being eluted are freed in some manner such that they can be eluted and recovered.

In accordance with some embodiments, a trapping module of a MACS system includes a channel through which a sample, including species attached and not attached to magnetic particles flow. One side of the channel includes a magnetic field gradient generating structure that generates a magnetic field gradient with the application of a magnetic field from an external source. This magnetic field gradient attracts and captures magnetic particles along with the attached species. After the sample flows through the trapping module, the captured particles may be released by changing the applied magnetic field or by cleaving the link between the magnetic particles and the attached species.

For example in certain embodiments, a fluidic separating device may be characterized by the following features: (a) at least one sample inlet or access channel configured to provide a sample stream in the fluidic separating device; (b) at least one sheath flow inlet channel configured to provide one or more fluid streams that form a sheath around the sample stream within the fluidic separating device, and thereby reduce nonspecific binding of components of the sample to the device; (c) a sorting station fluidly coupled to the sample and sheath flow inlets and located along a path of the sample stream; and (d) a magnetic field gradient generator for interacting with an external magnetic field to produce a change in magnetic field gradient in the sorting station and thereby deflecting and/or trapping magnetic particles from the sample stream.

In some cases, the sorting station has a substantially rectangular interior space for bounding fluid flowing through the sorting station. In such cases, the interior space has first and second lateral dimensions transverse to (e.g., perpendicular to) the sample stream's direction of flow. In various embodiments, the second lateral dimension (which is often a width on the horizontal plane) is at least about 2 times larger than the first lateral dimension (which is often a height in the vertical direction). The device may be configured such that the at least one sheath flow inlet channel is configured to provide two sheath streams separated from one another by the sample stream along the first lateral dimension.

Further, in some embodiments employing an interior rectangular space, the interior space is defined, in part, by two substantially parallel and substantially planar surfaces separated by a distance not greater than about 2 millimeters, and in other cases not greater than about 1 millimeter. In such embodiments, the at least one sheath flow inlet channel is configured to provide two sheath streams flowing in contact with the two parallel planar surfaces and separated from one another by the sample stream. A first sheath flow inlet channel may include a substantially planar surface located upstream of the sorting station and oriented substantially parallel to the two substantially planar surfaces of the interior space. Additionally, the device may include a second sheath flow inlet channel, having its own substantially planar surface located upstream of the sorting station and oriented substantially parallel to the two substantially planar surfaces of the interior space. The sample inlet channel may have its own substantially planar surfaces parallel to the two substantially parallel and substantially planar surfaces of the sorting station interior space. These surfaces may be provided on planar structures that also provide planar surfaces employed in the sheath flow inlet channels. Exemplary structures are depicted in FIGS. 1, 2 and 6A-6C.

The magnetic field gradient generator of the fluidic separating device may include a plurality of ferromagnetic elements patterned on the sorting device proximate the sorting station, and may have a permanent magnet proximate the plurality of ferromagnetic elements. The plurality of ferromagnetic elements may be disposed within a fluid pathway of the sorting station to allow fluid contact between the ferromagnetic elements and the sample stream. It may be desirable to provide a protective or passivating layer over the ferromagnetic elements in order to prevent the elements from coming in direct contact with the flowing sheath and sample. Such layer is useful to prevent, e.g., poisoning or contamination of sample components such as cells. Examples suitable protective layers include thin (e.g., 10 nm to 1 micrometer) layers of silicon oxide, silicon nitride, or other suitably inert barrier material. In certain embodiments, the ferromagnetic elements include nickel elements such as micropatterned elements. Examples are set forth in FIGS. 8A-8H. As shown, the ferromagnetic structures are provided in an organized or a random pattern, such as parallel lines, an orthogonal grid, and rectangular arrays of regular or irregular geometric shapes. The structures may be regular or reticulated as shown. In a specific example, nickel ferromagnetic elements are coated with a thin silica passivating layer. In various embodiments, the magnetic field gradient generator is configured to temporarily capture the magnetic particles and then release the magnetic particles.

As described above in relation to FIGS. 2A and 2B, ferromagnetic structures are formed on the inside surface of a lower wall of a flow channel. These serve as a magnetic field gradient generating (MFG) structures. An external magnetic field is typically used as the driving force for trapping the magnetic particles flowing through the fluid medium. The MFG structures may shape the external magnetic field in order to create locally high magnetic field gradients to assist capturing flowing magnetic particles. In the depicted embodiment of FIG. 2A, the external magnetic field is provided by an array of permanent magnets of alternating polarity. More generally, the external magnetic field may be produced by one or more permanent magnets and/or electromagnets. In some embodiments, a collection of magnets such as those shown in FIG. 2A are moveable, individually or as a unit, in order to dynamically vary the magnetic field applied to the trapping region.

In certain embodiments, the magnetic field is controlled using an electromagnet. In other embodiments, permanent magnets may be used, which are mechanically movable into and out of proximity with the sorting station such that the magnetic field gradient in the sorting region can be locally increased and decreased to facilitate sequential capture and release of the magnetic particles. In some cases using an electromagnet, the magnetic field is controlled so that a strong field gradient is produced early in the process (during capture of the magnetic particles) and then reduced or removed later in the process (during release of the particles).

Figure 3A:
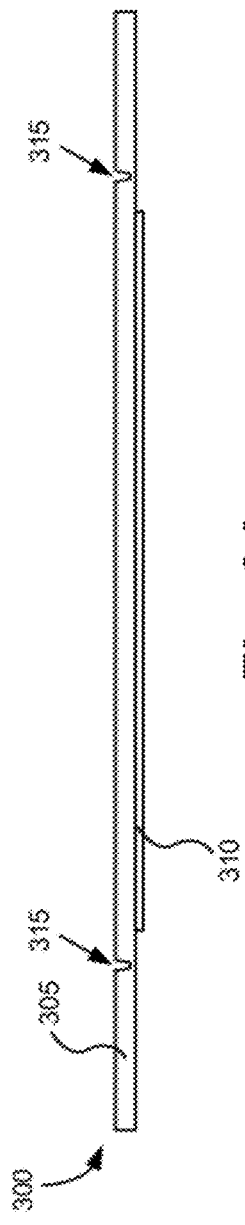
FIGS. 3A and 3B are illustrations presenting a cross-sectional side view and a top view, respectively, showing a removable magnetic trapping station.
Figure 3B:
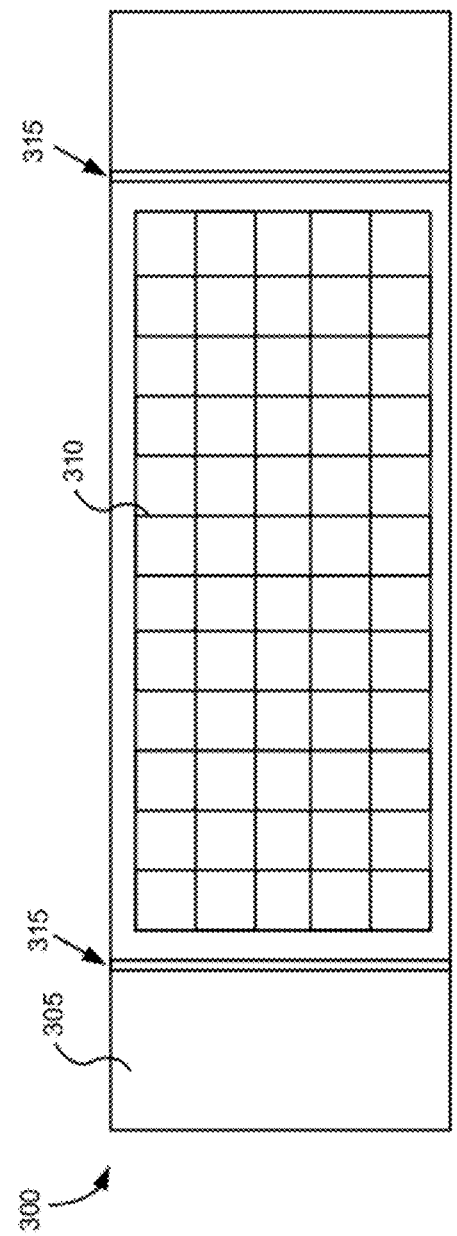

In one embodiment, the trapping region of the device is removable. In another embodiment, the removable trapping region is disposable. In a specific embodiment, where the plate incorporating the trapping region, e.g. a nickel grid, is disposable, the trapping region is defined by an outermost perimeter that is scored such that after the trapping operation and washing to remove any waste, the trapping region can be "snapped" out of the plate incorporating the trapping region. This is depicted in FIGS. 3A and 3B, a side view and top view of a plate, 300, incorporating a nickel grid trapping region, 310, and scores, 315, in the plate such that, for example, a suction cup device can be used to pull the removable trapping region from the plate by applying force pulling force sufficient to break along the scores in the plate. The removable trapping region can be removed with or without the magnetic field applied, depending on the need. Once removed, target cells can be analyzed or manipulated on the grid or removed and analyzed or manipulated off the grid.

As shown in the example of FIG. 2A, the magnetic particles are coated with one or more molecular recognition elements (e.g., antibodies) specific for a marker of a target cell or other species to be captured. Thus, one or more magnetic particles, along with a bound cell or other target species, flow as a combined unit into the trapping module. For large target species having many exposed binding moieties (e.g., mammalian cells), it will be common to have multiple magnetic particles affixed.

In some embodiments, the trapping region is relatively thin but may be quite wide to provide relatively high throughput. In other words, the cross-sectional area of the channel itself is relatively large while the height or depth of the channel is quite thin. The thinness of the channel may be defined by the effective reach of the magnetic field which is used to attract the magnetic particles flowing through the trapping region in the fluid medium. In some embodiments, therefore, the cross-sectional height of the trapping region interior is about 2 millimeters or less. In some cases, the height is about 1.5 millimeters or less, or about 1 millimeter or less, or even about 0.8 millimeters or less. The width of the trapping region interior space is dictated by a combination of throughput considerations and fabrication limitations. In some embodiments, the width is less than 1 millimeter, but can be larger than 30 cm. In a specific example, the height is about 0.5 to 1 millimeter and the width is about 15 to 25 centimeters. Further, throughput may be improved by connecting multiple separate sheath flow trapping devices in parallel. In some embodiments, a single sample supply feeds each of these parallel devices. Similarly, a single supply of buffer or other sheath flow fluid may feed the devices. The number of such devices operated in parallel may be 2, 3, 4, 5, or even more.

Various details of fluidics systems suitable for use with this invention are discussed in other contexts in the description of flow modules in U.S. patent application Ser. No. 11/583,989, published as US 2008/0124779A1, entitled, "Microfluidic magnetophoretic device and methods for using the same," filed Oct. 18, 2006, naming Sang-Hyun Oh, et al. as inventors, which is incorporated herein by reference for all purposes. Examples of such details include buffer composition, magnetic particle features, external magnet features, ferromagnetic materials for MFG's, flow conditions, sample types, integration with other modules, control systems for fluidics and magnetic elements, binding mechanisms between target species and magnetic particles, etc. Generally, in a magnetic trapping module the applied external magnetic field will be relatively higher (considering the overall design of the module) than that employed in a continuous flow magnetic flow sorter of the type described in U.S. patent application Ser. No. 11/583,989 (supra). In any event, the magnetic force exerted on target species should be sufficiently greater than the hydrodynamic drag force in order to ensure that the target species (coupled to magnetic particles) are captured and held in place against the flowing fluid.

Figure 8:
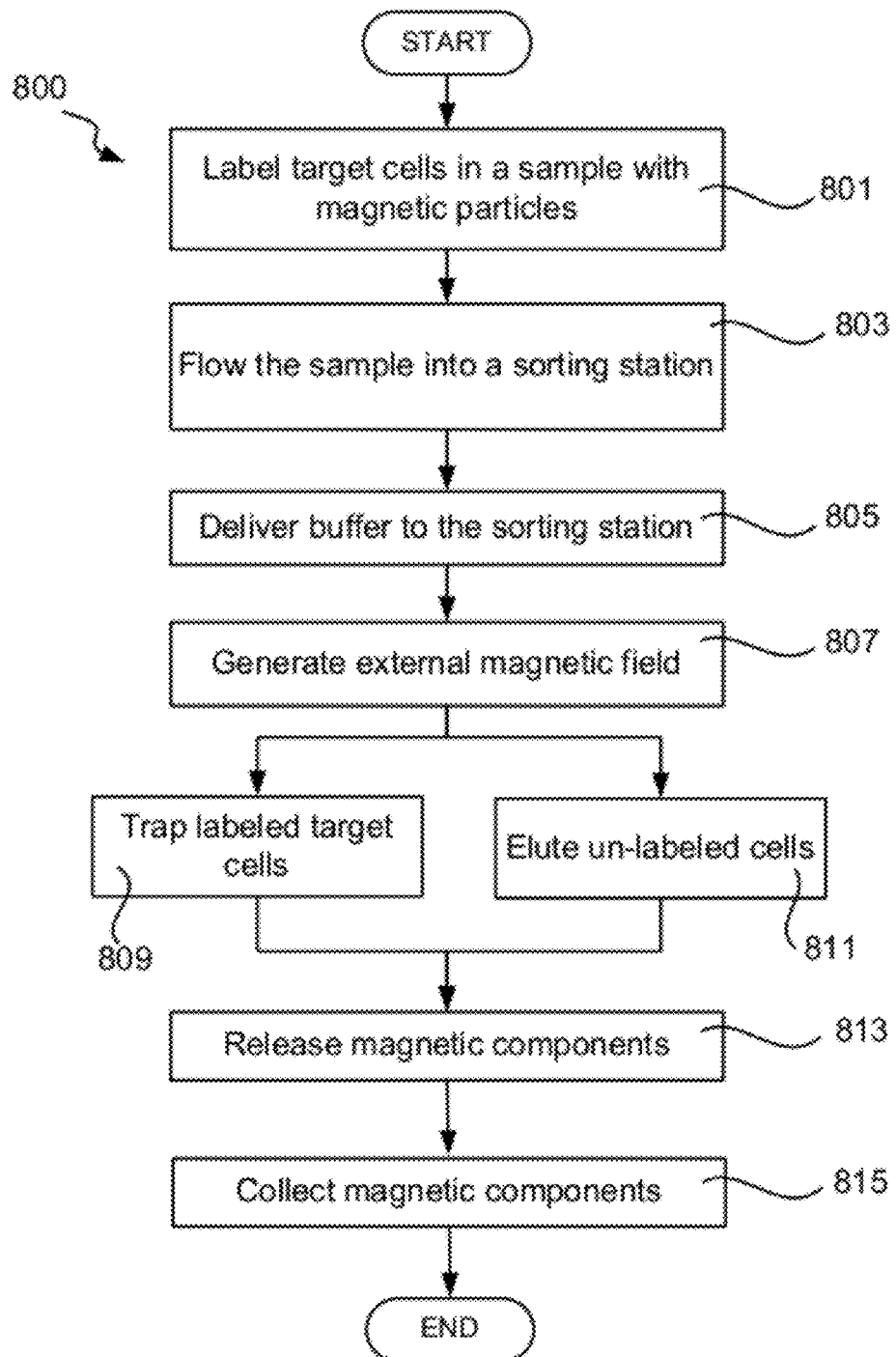
FIG. 8 is a process flow diagram of a method of sorting a sample in accordance with various embodiments.

In a typical positive selection example as shown in FIG. 8, a magnetic trapping process 800 proceeds as follows. First, a sample such as a biological specimen potentially containing the target cells are labeled with small magnetic particles coated with a capture moiety (e.g., an antibody) specific for the surface marker of the target cell in operation 801. This labeling process may take place on or off the microfluidic sorting device. After this labeling, the sample is flowed into the sorting station (including a trapping region) with or without concurrently flowing buffer solution in operation 803. Buffer may be delivered through one or more sheath flow inlets and sample through one or more others, see 805. In a specific embodiment, buffer is flowed first to establish a sheath flow of one or two laminar flows of buffer. One laminar flow of buffer is used to prevent unspecific binding to an internal surface of the device in proximity to the sorting station. When two laminar buffer flows are used, one is used as described above and the other to protect another internal surface of the device from unspecific binding, where the sample laminar flow is between the two buffer laminar flows. The sorting station is energized with an external magnetic field in operation 807 to hold the magnetically labeled target cells or other species in place against the hydrodynamic drag force exerted by the flowing fluid in operation 809. This occurs while continuously eluting the un-labeled non-target species in operation 811. As explained above, the magnetic field is typically applied by an external magnet positioned proximate the sorting station. After most, or all, of the sample solution has flowed clear of the sorting station, the magnetic components may be released in operation 813 by any of a number of different mechanisms including some that involve modifying the magnetic field gradient and/or increasing the hydrodynamic force. For example, the magnetic field in the chamber may be reduced, removed, or reoriented and concurrently the sample inlet flow is replaced with release agent (for releasing the captured species) and/or buffer flow. Ultimately the previously immobilized magnetic components, or just their captured species (now purified), flow out of the chamber in a buffer solution. The purified sample component including the target species may then be collected at an outlet of the sorting chamber in operation 815, which, in some configurations may be located directly downstream from the trapping chamber. In some cases, the purified target species are delivered to one or more post-processing stations. Then the process flow ends.

In some embodiments, the trapped target material is directly removed from the trapping region. The material so removed can be analyzed, used to produce cell products, manipulated for other purposes, etc. In one case, the trapping region of the device is designed to be peeled away, with trapped material attached, from the remainder of the device. To this end, the device may be designed with a thin perimeter or weakened region around the magnetic field gradient generating region. With this configuration, a technician can detach the trapping region to provide external access to the trapped material after the sample has passed through the device. To facilitate the detachment process, the device may be designed with mechanical design provisions such as tabs, notches or ridges.

For context an example of a trapping-type magnetic separation system will now be described. The system employs disposable fluidics chips or cartridges, each housing fluidics elements that include a magnetic trapping module. In one mode of operation (positive selection), a sample such as a small quantity of blood is provided to a receiving port in the cartridge and then the cartridge with sample in tow is inserted into a processing and analysis instrument. Within the chip, the magnetic particles and the target species (if any) from the sample are sorted and concentrated at the magnetic trapping module. After sample has been processed in this manner, trapped species may be released and collected in output tubes. This may be accomplished by various means including reducing or eliminating the external magnetic field applied to the trapping module or applying a reagent that releases captured species from magnetic particles. Alternatively, or in conjunction, the hydrodynamic force exerted on the magnetic particles may be increased. In certain embodiments, a chassis houses the system components including a pressure system (such as a syringe pump and a pressure controller) that provides the principal driving force for flowing sample through the trapping module. Of course, other designs may be employed using alternative driving forces such as a continuous pump or a pneumatic system. Buffer from buffer reservoirs is also provided to the cartridge under the controlled by a buffer pump and a flow control module.

Sheath Flow Device Manufacturing Systems: In general, the present devices and related instrumentation may be manufactured according to available methods, so long as configuration to allow a laminar flow establishing surface is a component.

Lithography and etching technologies may be used to manufacture the precise design for desired microfluidic flow. At a reduced cost, one may use injection molding for preparation of a rigid base having a particular configuration. Preparing the base alone, however, leaves the chambers and channels (in which the liquid flows) open. To enclose the device, one may then seal a top layer of similarly rigid material using laminate, heat, acoustic or laser (to adhere a top layer for a sealed device).

Materials, such as glass, vinyls or other conventional plastic polymers, may be used for "lab on a chip" and other devices. The cartridge design (channels, inlets, compartments and other fluid flow paths or containment areas) may be configured. Interconnection elements, such as ports use for inlet or outflow, or for pressurized flow/stoppage, may be attached, or formed as part of the injection molded design (for example). Other elements, such as electro-, mechanical, or various sensors may be in similarly dedicated location.

The present sheath flow device manufacturing systems include apparatuses for fluid fill, assembly, separating, coding (such as bar coding), sterilizing, and packaging.

The present manufacturing systems include those in compliance with various governmental or industry regimes, including food and drug requirements (e.g., FDA, EMEA), quality control organizations (e.g., International Organization for Standardization), and other regimes set up to ensure quality for a particular purpose.

Sheath Flow Device Instrumentation Systems: The present devices and methods may be adapted or configured to work in conjunction with host instruments or to meet system requirements. Adaptations or configurations include (but are not limited to) one or more for vacuum filling, automated control of pumps and valves, pressure flow, injection loop for sample loading, temperature control, electro-osmotic flow, positive displacement pumping, expected volumetric flow rate, centrifugal force processes, humidity control, and gas exchange control, for example.

Fluid flow may be controlled by automated instrumentation, although depending on the device, one may use manual control. Devices of the present invention, for example, can use pneumatic or air pressure, to establish flow via integrated ports operably linked with automated instrumentation.

Processing Prior to Trapping:

Various processes may be performed "upstream" from or prior to sorting in a sheath flow device. Examples of these processes include target labeling, cell lysis, and depletion. Labeling as explained in the following discussion may involve coupling magnetic particles having specific binding moieties to target or non-target components of a sample. Lysis may involve breaking cell membranes or cell walls to release cell components (organelles, biomolecules, etc.) into the sample. Depletion involves removing a particular component or components in a sample prior to separation. An example of depletion is removal of erythrocytes from a sample by acoustic or other means. Other pre-processing operations that may be performed on- or off-chip include a variety chemical means for staining, fixing or introducing exogenous materials into the cells.

In many implementations, it is necessary to insure that the target or non-target components of a sample become "labeled" with magnetic beads as appropriate. This labeling operation is performed upstream (prior to) the trapping/separating stage in which the magnetic particles are captured and held stationary in a flowing fluid medium.

The magnetic particles will have a surface functional group that has a specific affinity for either the target or non-target species. Thus, when the magnetic particles come in contact with the relevant species, they bind with those species to form conjugates. An inventive operation pertains to a mechanism for facilitating the binding or conjunction of the magnetic particles with the appropriate species or component from the sample.

Typically, though not necessarily, this pre-sorting treatment is performed in one or more separate chambers or reservoirs located in fluid communication with the trapping region. Such chambers or reservoirs may be located on the same device (chip) as the trapping region or in a separate device or chip. They may have micro fluidic dimensions or even slightly larger dimensions if appropriate. In one example, each of one or more pre-treatment reservoirs has a volume of approximately five milliliters. In some cases, the reservoirs may be between 0.5 ml to 10 ml.

The magnetic beads, as well as the sample, and other reagents to facilitate binding are each provided to the reservoir or reservoirs. Note that the magnetic particles may be provided in a functionalized form, in which case it will be unnecessary to provide the other reagents. The magnetic particles are moved with respect to the other components in the reservoir(s) to facilitate labeling. This movement is induced by successive application of pneumatic pressure two separate chambers in accordance with certain embodiments. In some embodiments, this movement is induced by a magnetic mixing mechanism of the type described for magnetic particle release as described in a later section. The same mechanisms for facilitating mixing may be employed; e.g., a moving a magnetic field as by, for example, oscillating the field. Other examples of mixing mechanisms include ultrasonic agitation or stirring. Examples of systems and methods that provide fluidic mixing of magnetic particles and allow for labeling and/or release of sample species are described in detail in PCT Patent Application No. PCT/US2009/040866, filed Apr. 16, 2009 (PCT Publication No. WO 2009/129415), incorporated herein by reference for all purposes.

Processing After Trapping:

Various processes may be performed after sorting in a sheath flow device. These processes may be performed in the sorting station and/or downstream from the station. Generally, the processes may involve quantifying target species (e.g., counting cells), extracting molecular information about the target species (e.g., whether a particular SNP is present), and/or extacting cell based products (e.g., a differentiated version of trapped stem cell). Examples of suitable processes include direct detection of target species as by optical techniques, assaying, growth of trapped cells or viruses, transformation of the target species (e.g., differentiating trapped stem cells), profiling expression patterns, and genetic characterization. Specific tools that may be employed to characterize expression profiles and/or genetic sequences include microarrays such as mRNA arrays and high throughput sequencing tools. Further discussion may be found in PCT Patent Application No. PCT/US2009/040866 (supra).

Often post separation operations involve methods for releasing target species from magnetic particles that have been trapped in a trapping station or otherwise separated in a sorting station. In a typical scenario, at the end of a trapping operation, the only sample species that remain in the trapping region are bound to magnetic particles. For many applications, it is important to separate the captured species from the magnetic particles prior to further processing.

In the post separation operations described here, some mechanism for releasing the bound species from the magnetic particle is employed. Various binding and release systems are available. These include, for example, release reagents that (1) digest a linkage chemically coupling the magnetic bead to the captured species, (2) compete with chemical or biochemical linkage mechanisms for binding with the captured species, and (3) cleaving the linkage with a secondary antibody.

Trapped target species may be simply concentrated, purified and/or released as described. Alternatively they can be further analyzed and/or treated.

In some embodiments, the particles that have been captured and washed and optionally released in the trap as described above are exposed to one or more markers (e.g., labeled antibodies) for target species in the sample. Certain tumor cells to be detected, for example, express two or more specific surface antigens. To detect these tumors, more than one marker may be used. This combination of antigens occurs only in certain unique tumors. After one or more labels flow through the trap for a sufficient length of time, the captured particles/cells may be washed. Thereafter, the particles/cells can be removed from trap for further analysis or they may be analyzed in situ. For example, the contents of trap may be scanned with probe beams at excitation for the first and second labels if such labels or fluorophores for example. Emitted light is then detected at frequencies characteristic of the first and second labels. In certain embodiments, individual cells or particles are imaged to characterize the contents of trap 301 and thereby determine the presence (or quantity) of the target tumor cells. Of course various target components other than tumor cells may be detected. Examples include pathogens such as certain bacteria or viruses.

In another embodiment, nucleic acid from a sample enters is captured by an appropriate mechanism. These nucleic acids can be detected and profiled directly without any amplification, for example using microarrays. Alternatively, PCR reagents (nucleotides, polymerase, and primers in appropriate buffers) enter the trap and an appropriate PCR thermal cycling program is performed. The thermal cycling continues until an appropriate level of amplification is achieved. Subsequently in situ detection of amplified target nucleic acid can be performed for, e.g., genotyping or detection of a particular mutation. Alternatively, the detection can be accomplished downstream of the trap in, e.g., a separate chamber which might contain a nucleic acid microarray or an electrophoresis medium. In another embodiment, real time PCR can be conducted in trap by introducing, e.g., an appropriately labeled intercalation probe or donor-quencher probe for the target sequence. The probe could be introduced with the other PCR reagents (primers, polymerase, and nucleotides for example). In situ real time PCR is appropriate for analyses in which expression levels are being analyzed. In either real time PCR or end point PCR, detection of amplified sequences can, in some embodiments, be performed in the trap by using appropriate detection apparatus such as a fluorescent microscope focused on regions of the trap.

In some embodiments, capture elements capture and confine cells from sample to reaction chamber in situ. Thereafter, a lysing agent (e.g., a salt or detergent) is delivered to the chamber. The lysing agent may be delivered in a plug of solution and allowed to diffuse throughout the chamber, where it lyses the immobilized cells in due course. This allows the cellular genetic material to be extracted for subsequent amplification. In certain embodiments, the lysing agent may be delivered together with PCR reagents so that after a sufficient period of time has elapsed to allow the lying agent to lyse the cells and remove the nucleic acid, a thermal cycling program can be initiated and the target nucleic acid detected.

In other embodiments, sample nucleic acid is provided in a raw sample and coupled to magnetic particles containing appropriate hybridization sequences. The magnetic particles are then sorted and immobilized in the trap. After PCR reagents are delivered to the chamber and all valves are closed, PCR can proceed via thermal cycling. During the initial temperature excursion, the captured sample nucleic acid is released from the magnetic particles.

The nucleic acid amplification technique described here is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA). Each of these can be performed in a trap such as a chamber in the device containing appropriate valving and flow lines.

Besides the extraction and analysis of the nucleic acids, the captured cells themselves may be used directly as the product of the process, or they can be manipulated to produce the desired product. For example, the device may be used to isolate stem cells from blood or tissue as the cell-based product. Alternatively, the captured cells may be manipulated with reagents such as growth factors, chemokines, and antibodies to produce the desired cell- or molecule-based products. Multiple processes of purification and manipulation may be performed to obtain the desired product within the device.

One example operation employing the apparatuses and methods of the present invention is automated protein purification, particularly as protein is expressed in cell culture. Protein purification may be performed manually. However, the apparatuses and methods of the present invention provide a time and labor saving automation that delivers a high purity product with low cost.

In one example, desired proteins are expressed in organisms such as virus, bacteria, insect or mammalian cells. The expressed protein may be designed such that it may be selectively isolated from background materials. This may be accomplished via adding one or more selectable amino acid tags that add a stretch of amino acid to the protein. The tag may be a His tag, FLAG tag or other epitope-based tags (E-tags). The cells (for example) are introduced to one of the sample reservoirs described herein, with magnetic particles and lyses reagents in the same or one or more reservoirs. The magnetic particles may be magnetic beads coated with a high affinity media such as NTA-agarose or other resin containing to nickel. Mixing between the various sample reservoirs is promoted via one or more of the techniques described above, e.g., pneumatic, hydraulic, or magnetic mixing. The cells are disrupted by the lysing reagent and, under suitable conditions, the magnetic particles bind with the target protein in the lysate. The raw lysate is then flowed into the magnetic separation chamber where the beads become trapped on the surface of the channel. Wash buffer is added to elute the untagged and unbound protein and other cell fragments. According to various embodiments, the magnetic separation chamber may be agitated magnetically or through other means to further remove any unbound protein stuck between trapped particles. A highly stringent wash buffer may be used to further elute unwanted particles. At this point, only the target protein and bound magnetic particles remain in the chamber with very high selectivity. The target protein may be released by using a bead release agent into a small volume, optionally for further processing. Lastly, the magnetic particles may be released. Because these various operations occur on a unitary or disposable cartridge in a machine, the procedure may be preprogrammed and automated to save time and cost. This configuration may be used to selectively trap other nucleic acid related products, such as RNA, which may be so labeled so as to be similarly selectable.

General Applications:

As explained, the sheath flow devices of this invention are widely applicable. They may be used to capture and separate many different types of target species tagged with magnetic particles. Thus the sheath flow fluidic devices of this invention have many applications including, for example, biological fluid sample preparation and analysis, separation of rare molecules or cells, chemical library screening, point of care diagnostic in a clinical laboratory setting, environmental testing or monitoring, consumer products and food quality control aspects. The invention finds particular application in academic, industrial and clinical settings. In academic, industrial and clinical settings, sheath flow devices of the invention find particular use in isolating cell lines, proteins, genetic material and the like for testing, characterization and further manipulation, for example amplification of cell lines, proteins, mRNA, genetic code, molecular signature proteonomics and the like. Sheath flow devices and methods can be used in early detection and diagnosis of disease, for example cancers via isolation of CTC's from blood samples. In clinical settings in particular, embodiments include screening potential patient pools for clinical trial candidacy and/or testing biological fluids of patients already enrolled in clinical trials for information on therapy efficacy and/or future course of treatment regimens as well as measuring the efficacy of adjunct therapy or neo-adjunct therapy. More specific examples are described below.

Sheath Flow Research Tools:

The present sheath flow devices have broad use in scientific research, including but not limited to screening molecular libraries. For example, one can use the present devices for screening aptamer libraries by preparing a purified and isolated protein on the present device, and then exposing the protein to an aptamer library, within a single device. The term "aptamer" as used herein is meant in its broadest sense to denote oligonucleic acid or peptide molecules which bind to a specific target molecule, and related synthetic molecules, such as mimetics. Sheath flow devices of the invention can be used for biomarker/drug discovery platforms that utilize molecular or cellular library sorting such as aptamer library, ribosome library, phage display, bacterial peptide display, yeast display systems and the like. In another example, sheath flow devices of the invention can be used to isolate target cells for a variety of endpoints including cell count, typing, amplification, differentiation and the like.

Sheath Flow Bio/Chemical Monitoring, Synthesis or Analysis: The present invention may be configured or adapted for a variety of biological or chemical monitoring, synthesis or analysis purposes, such as, for example, chemical threat monitoring, nucleic acid analysis (and amplification using, for example, polymerase chain reaction), continuous monitoring of particular conditions, such as closed environmental monitoring, personalized genomics and diagnosis, chemical synthesis, such as synthesis of aptameric therapeutics contained within viral coats or other nanocages suitable for delivery into a physiologic environment, or other chemical syntheses. For home use, for example, in monitoring swimming pool or drinking water quality, one may include pH indicator, metal indicators, or other indicators of water quality. The present devices can be configured or adapted for production process control, such as bioreactor monitoring in biopharmaceutical production processes, or for the food industry. The present devices can be adapted or configured for fluid control and analysis, gas control and analysis. For example, by adapting the present devices for continuous flow, one can monitor the rate at which cells are sorted. The present devices can be configured for production quality control, such as for supply chain monitoring. Since sheath flow apparatus of the invention can capture target species from liquid samples with high selectivity, this represents a strong advantage over many conventional systems where, for example in therapeutic settings, a target species must be isolated in high purity from a fluid biological sample having a highly complex mixture of species.

Configurations:

Prefilled "Kit on a Chip" Because of the ease in manufacture and use, it is contemplated that one aspect of the present invention is a sheath flow device prefilled with reagents useful for a particular purpose. For example, devices may be prefilled with reagents useful for biological sample preparation. This "kit on a chip" sheath flow device aspect can be adapted for a variety of applications as described above.

Such "kit on a chip" embodiments may include a variety of reagents and may be adapted for a variety of fields, such as biological fluid sample preparation and analysis, separation of rare molecules or cells, chemical library screening, point of care diagnostic in a clinical laboratory setting, environmental testing or monitoring, consumer products and food quality control aspects, for example. The present invention includes single or a plurality of prefilled devices suitable for such uses. Configurations are non-limiting, but should be considered along with related instrumentation and methods.

Reagents can be disposed within the sheath flow device for ease of use, for example in reservoirs in predetermined amounts. For example, a substantially purified protein preparation may be obtained by culturing cells so expressing the desired protein. The subject reservoir may be so adapted to culturing the cells, and have access ports with appropriate reagents in fluidic communication under controlled conditions. Reagents include buffers for lysing cells, washing cells, and removing beads selectively bound to a moiety. Additional reagents include selective binding molecules, such as antibodies, aptamers, and other molecules that selectively (although not necessarily specifically) bind a target molecule. Further reagents include various moieties allowing capture of the selected molecule, such as magnetic beads, acoustic beads and other beads providing that function. Reagents further include nucleic acids such as primers suitable for selecting particular nucleic acids from a complex mix. For example, the present device may be used to screen genomic DNA, and amplify selected sequences using polymerase chain reaction, within the device itself.

Integrated Systems: A kit on a chip configuration can stand alone, be part of or serve as an integrated system that contains sheath flow devices of the invention. Additional processing modules or chambers can be added "upstream" or "downstream" of the sheath flow component of apparatus of the invention. For example, one can prepare suitable post-expression modification fluidic circuitry, such as providing reservoirs with, for example a desired polymeric or other substance for derivatization and or other reaction. In a specific example, the present sheath flow device is configured with fluidic circuitry for protein expression from cells in culture, and optionally additional modules for derivatizing the protein so expressed, such as a pegylation module in which one may derivatize the subject protein.

Examples of operational modules that may be integrated with magnetic trapping sorters in fluidics devices include (a) additional enrichment modules such as fluorescence activated cell sorters and washing modules, (b) reaction modules such as sample amplification (e.g., PCR) modules, restriction enzyme reaction modules, nucleic acid sequencing modules, target labeling modules, chromatin immunoprecipitation modules, crosslinking modules, and even cell culture modules, (c) detection modules such as microarrays of nucleic acids, antibodies or other highly specific binding agents, and fluorescent molecular recognition modules, and (d) lysis modules for lysing cells, disrupting viral protein coats, or otherwise releasing components of small living systems. Each of these modules may be provided before or after the magnetic sorter. There may be multiple identical or different types of operational modules integrated with a magnetic sorter in a single fluidics system. Further, one or more magnetic sorters may be arranged in parallel or series with respect to various other operational modules. Some of these operational modules may be designed or configured as traps in which target species in a sample are held stationary or generally constrained in a particular volume. Features of operational modules depend on the type of reaction desired and may include a thermal management system, micromixer, catalyst structure and sensing system. A thermal management system may include heaters, temperature sensors, and micro heat exchangers. All these components may be integrated to precisely control temperatures. Such temperature control is crucial for example when using PCR for DNA amplification.

As should be apparent from the above examples of modules, operations that may be performed on target and/or non-target species in modules of integrated fluidics devices include sorting, coupling to magnetic particles (sometimes referred to herein as "labeling"), binding, washing, trapping, amplifying, removing unwanted species, precipitating, cleaving, diluting, ligating, sequencing, synthesis, labeling (e.g., staining cells), cross-linking, culturing, detecting, imaging, quantifying, lysing, etc. The present devices may be configured to perform one of more functions within the same device.

Examples of biochemical operations that may be performed in the magnetic sorting modules of integrated sheath flow fluidic devices include synthesis and/or screening of plasmids, aptamers, proteins, and peptides; evaluating enzyme activity; and derivatizing proteins and carbohydrates. A broad spectrum of biochemical and electrophysiological assays may also be performed, including: (1) genomic analysis (sequencing, hybridization), PCR and/or other detection and amplification schemes for DNA, and RNA oligomers; (2) gene expression; (3) enzymatic activity assays; (4) receptor binding assays; and (5) ELISA assays. The foregoing assays may be performed in a variety of formats, such as: homogeneous, bead-based, and surface bound formats. Furthermore, devices as described herein may be utilized to perform continuous production of biomolecules using specified enzymes or catalysts, and production and delivery of biomolecules or molecules active in biological systems such as a therapeutic agents. Sheath flow devices as described herein may also be used to perform combinatorial syntheses of peptides, proteins, and DNA and RNA oligomers as conventionally performed in macrofluidic volumes.

Specific Applications:

Cell Trapping and Manipulation: As indicated above, exploitation of the present sheath flow devices is particularly useful when configured or adapted for culturing, purifying or isolating components of, or analyzing a variety of biological materials. In particular aspects, the present devices may be configured or adapted for cell lysis, bead-based displacement assays, perfusion, filtration, sample preparation, chemotaxis, whole blood separation, and a variety of other processes.

Isolation of particular cell types from a complex biological sample is particularly useful. For example, a biological sample may contain one or more stem cells, bacteria, human cells, bio-film materials, mammalian cells, yeasts, algae, primary tumor cells, immortalized cell lines, tissue or organ cultures, unicellular or multi-cellular organisms, molds and other organisms that can be isolated from the sample, for example a culture. Conventionally, isolating cell types from these complex mixtures is labor intensive and often unsuccessful due to low yield, low purity, nonviability of isolated cells due to excessive manipulation, and the like. As mentioned, sheath flow devices of the present invention may not only have fluidic circuitry adapted for cell sorting but also isolation of different cell types which can subsequently be expanded or differentiated for use in characterization, therapy and the like. Sheath flow apparatus of the invention allow post-isolation processes such as expansion and differentiation ex situ and/or in situ.

Target cell types are isolated by, for example, tagging the cells with magnetic particles that bear a binding agent, for example an antibody or chemically reactive group, selective for the target cell. The sample is exposed to the magnetic particles and thus the target cells are selectively bound to the magnetic particle via the selective binding agent bound to the magnetic particle. Two exemplary cell types where the sheath flow devices of the invention find particular use are stem cells and circulating tumor cells (CTC's). A more detailed description of applications of sheath flow devices and methods for stem cells and CTC's follows.

Stem Cells: Medical researchers believe that stem cell treatments have the potential to change the face of human disease and alleviate suffering. The propensity of stem cells to self-renew and generate new stem cell populations offers an enormous potential for repairing and/or replacing (via differentiation to the target cell population) diseased and damaged tissues in the body, without the risk of rejection and side effects. Medical researchers anticipate using adult and embryonic stem cell technology to treat cancer, metabolic disorders, cardiac failure, muscle damage and neurological disorders. More specific disorders for which stem cell therapies show promise are brain damage, cancer, spinal cord injury, heart damage, haematopoiesis, baldness, missing teeth, deafness, blindness and vision impairment, amyotrophic lateral sclerosis, graft v. host disease, Crohn's disease, neural and behavioral birth defects, diabetes, orthopedic disorders, wound healing and infertility. See: *The Leading Edge of Stem Cell Therapeutics*, by Singec I., et al., Annu Rev. Med. 58: 313-328, 2007.

A key to stem cell research and/or treatments is the isolation of highly pure viable stem cells. As described above, sheath flow apparatus and methods of the invention allow a user to select and isolate particular stem cells, for example, from blood, marrow, umbilical cord or other sources, and optionally, carry out further manipulation of the isolated cells, for example, culturing the cells isolated by the sheath flow device in situ and/or ex situ.

Thus one particular aspect of the invention are sheath flow devices and methods configured for isolating stem cells from a biological sample. Such selective binding molecules can be connected to a variety of suitable vehicles for selection within the sheath flow device, such as a magnetophoretic bead, an acoustic bead, or other moiety capable of capturing the molecule (and cell) so selected. In one embodiment, sheath flow devices use magnetic particles bearing moieties selective for stem cells, such as CD34+ selective binding molecules. In a particular embodiment, the magnetic particles are used to trap and isolate the stem cells by binding to the target stem cells, and while traveling in the sample stream surrounded by the buffer sheath flow of the device, are selectively pulled or deflected from the sample stream through the sheath flow to a collection grid.

The isolated stem cells can be characterized and/or manipulated on or off the collection grid. As mentioned, sheath flow devices of the invention may have additional post-isolation modules or features for amplifying stem cell populations and/or differentiating the stem cells. Post-isolation modifications can take place, for example depending upon the binding moiety and local environment, before or after separation from the magnetic particles used to trap the cells. Such post-isolation modules or features will have, as understood by one of ordinary skill in the art, additional features of a bioreactor for stem cell growth, such as media, oxygen, temperature, media replacement, and the like.

In a particular example, sheath flow devices of the invention can be configured for sorting suitable stem cells from blood, and further culturing the stem cells for expansion. One may optionally include selected media, growth factors, and other materials to be pre-filled on a present sheath flow device. For example, one may use hematopoietic stem cell selective reagents, such as antibodies or aptamers. Such reagents may selectively bind to, for example, CD34+ stem cells. In one example, the magnetic particles, bound and unbound to CD34+ cells, are then held in place, and other material is washed away. A bead release reagent, for example commercially available, is applied and the bound cells are released. While the beads are captured by the magnetic force, the stem cells may be separated in a fluidic supernatant. Other types of stem cells may include embryonic, fetal, amneonic, adult, or induced pluoripotent stem cells.

As described above, isolated cells, in this example stem cells, can be used to derive a cell based product from the stem cells separated from the liquid sample in the sheath flow device. Cell based products can include expanded cell populations, differentiated cells and products derived from analysis of molecular components of cells, for example, genetic coding information, RNA, DNA, oncogenic information and the like. In the context of stem cells, modules of the sheath flow devices of the invention can be used to culture stem cells, expanding and/or differentiating stem cell populations, either in situ, or removing them for expansion and/or differentiation in a different device. Expanded stem cell populations can be used for injection into a patient, for example at the site of a tumor or tissue damage, for example nerve or muscle tissue. Also stem cells can repair tissue or aid in repair of tissue. In oncology, stem cells can be used to aid in destruction of tumors. Additionally, cancer stem cells (CSC's) are thought to be a component of relapse of cancerous growths due to chemotherapy's ineffectiveness to kill CSC's while destroying tumorous growths. Sheath flow devices of the invention can be used to isolate, characterize and manipulate CSC's just as other stem cells described herein.

Sheath flow devices of the invention can also be used for tissue regeneration. For example, where the sheath flow device is used for stem cell expansion as describe above, reagents may be used to differentiate isolated stem cells into different types of tissue-related cells, another example of cell based product. Such sheath flow devices of the invention can be configured with biocompatible scaffolding and suitable reagents for growing tissues ex vivo. In one embodiment, a sheath flow device is configured to culture liver or other organ tissues, for transplant, based on cells originally isolated and grown in situ in the sheath flow device. As the present device may be configured for stem cell selection and in situ expansion, one may further configure the device, including pre-filled reagents, for various applications involving stem cell differentiation to a desired target tissue. The sheath flow device itself may be made of biocompatible material so that the stem cell-grown tissue (or population of cells on a scaffold) may be applied or implanted directly into a patient. In another example, the present sheath flow device can be configured to isolate stem cells and generate corneal tissue suitable for a corneal transplant.

Circulating Tumor Cells: A majority of cancer deaths are caused by haematogenous metastatic spread and proliferation of tumor cells in tissues throughout the body. Viable tumor derived epithelial cells, circulating tumor cells or CTC's, have been identified in peripheral blood from cancer patients and are likely the origin of intractable metastatic disease (see: Nagrath, S. et al. *Isolation of Rare Circulating Tumour Cells in Cancer Patients by Microchip Technology*, Nature, Vol 450: 20/27, 1235-1240, 2007). The study of CTC's is therefore highly relevant to the biology of early metastatic spread and provide a powerful diagnostic source in patients with overt metastases (see: Pantel, K., et al., *Detection, Clinical Relevance and Specific Biological Properties of Disseminating Tumour Cells*, Nature Reviews, Vol. 8: 329-40, 2008). Moreover, molecular analysis of CTC's from the blood of patients with cancer offers the possibility of monitoring changes in tumor genotypes during the course of treatment (see: *Detection of Mutations in EGFR in Circulating Lung-Cancer Cells*, Maheswaran, S., et al., N Engl J Med, 359:366-77, 2008). Therefore, utilizing liquid samples, for example from a simple blood draw, offers a huge advantage over invasive biopsies as a source of tumor tissue for the detection, characterization and monitoring of non-haematologic cancers.

A key to CTC research and/or treatments is the isolation of highly pure CTC's. Sheath flow apparatus of the invention allow a user to select and isolate CTC's from a liquid sample, for example from a blood draw, without having to biopsy solid tumors. Using apparatus and methods of the invention, one may select particular circulating tumor cells for analysis, for example from blood of a patient being diagnosed and/or monitored for a cell proliferation disorder such as cancer. Point of care diagnostics using sheath flow devices of the invention are a powerful tool for early and accurate diagnosis of, for example, cancer types and/or progression. Also, patients with existing cancers will benefit from a quick turnaround analysis of CTC's in their system, for example from a simple blood draw, for formulating current and future treatment regimens as well as measuring the efficacy of adjunct therapies such as surgery to remove a tumorous growth.

Thus one aspect of the invention is a method of monitoring and, if appropriate, adjusting a patient's treatment regimen, the method including: (a) receiving a sample including tumor cells from a patient undergoing a first treatment regimen; (b) separating the tumor cells from the sample by a separation method including: (i) labeling the sample with magnetic particles having a specific affinity for the tumor cells, thereby producing a labeled sample, (ii) passing the labeled sample through a fluidic device including a sorting region having a magnetic field gradient effective to deflect and/or trap the magnetic particles from the labeled sample and thereby separate the tumor cells from the sample, where the sample flows in a sheath of buffer solution to reduce nonspecific binding of the sample to the fluidic device; and (c) characterizing the tumor cells separated from the sample in (b) to suggest a future treatment for the patient and/or to assess the efficacy of an existing treatment. In one embodiment, the sample is a fluid sample taken from the patient. In a specific embodiment, the sample is a blood sample. In another embodiment, the tumor cells are CTC's. In one embodiment, the first treatment regimen is a chemotherapy regimen, and in a more specific embodiment, the future treatment is a different chemotherapy regimen. In one embodiment, characterization of the tumor cells is a count, in another embodiment characterization of the tumor cells is a molecular characterization. In a more specific embodiment, the molecular characterization is a genetic mutation in the tumor cells.

In one embodiment, suggesting the future treatment for the patient includes predicting a future effectiveness of the first treatment regimen. In another embodiment, suggesting a future treatment for a patient includes identifying a second treatment regimen that is different than the first treatment regimen and accounts for a characteristic of the tumor cells not previously observed for the patient. In another embodiment, the method further includes: (d) receiving a sample including tumor cells from the patient after the patient has undergone the second treatment regimen; and (e) thereafter performing (b) and (c) (as in the previous paragraph) on the sample and tumor cells received in (d).

Thus, using methods and apparatus of the invention, clinicians can, for example, screen a potential patient pool for candidates suitable for the clinical trials. In this way, patients, for example, having CTC's with oncogenic coding that indicates refractory response to intended treatment regimens can be steered towards other possible treatments. Or, in some cases refractory patients are specifically targeted for a particular new treatment regimen. In another example, a patient's CTC's are analyzed for a count and/or molecular components thereof, and from this information it is determined whether or not a current treatment is effective, should be continued, or another or additional treatments should be considered. In another embodiment, a patient's CTC's are analyzed by count and/or additional characterization to assess whether an adjunct therapy was efficacious. In a specific example, the patient's CTC count suggests that the adjunct therapy was successful and that no further treatment is currently necessary. In another specific example, the patient's CTC count suggests that the adjunct therapy was successful, but that another therapy is necessary based on a mutation in the CTC as compared to a previous CTC characterization from the patient. In another example, the patient's CTC count suggests that the adjunct therapy was unsuccessful, and that another adjunct therapy is indicated.

Embodiments

In accord with the description herein, one embodiment is a fluidic separating device including: (a) at least one sample inlet channel configured to provide a sample stream in the fluidic separating device; (b) at least one sheath flow inlet channel configured to provide one or more fluid streams that form a sheath around the sample stream within the fluidic separating device, and thereby reduce nonspecific binding of components of the sample to the device; (c) a sorting station fluidly coupled to the sample and sheath flow inlets and located along a path of the sample stream; and (d) a magnetic field gradient generator for interacting with an external magnetic field to produce a change in magnetic field gradient in the sorting station and thereby deflecting and/or trapping magnetic particles from the sample stream. In one embodiment, the magnetic particles are trapped by the sorting station.

In one embodiment, the sorting station has a substantially rectangular interior space for bounding fluid flowing through the sorting station, the interior space has first and second lateral dimensions transverse to the sample stream's direction of flow, the second lateral dimension is at least about 2 times larger than the first lateral dimension, and the at least one sheath flow inlet channel is configured to provide two sheath streams separated from one another by the sample stream along the first lateral dimension. In another embodiment, the sorting station has a substantially rectangular interior space for bounding fluid flowing through the sorting station, the interior space is defined, in part, by two substantially parallel and substantially planar surfaces separated by a distance not greater than about 2 millimeters, and the at least one sheath flow inlet channel is configured to provide two sheath streams flowing in contact with the two parallel planar surfaces and separated from one another by the sample stream. In one embodiment, the two substantially parallel and substantially planar surfaces are separated by a distance not greater than about 1 millimeter. In one embodiment, the at least one sheath flow inlet channel includes a first sheath flow inlet channel, which includes a substantially planar surface located upstream of the sorting station and oriented substantially parallel to the two substantially planar surfaces of the interior space.

In one embodiment, the fluidic separating device further includes a second sheath flow inlet channel, which includes its own substantially planar surface located upstream of the sorting station and oriented substantially parallel to the two substantially planar surfaces of the interior space. In one embodiment, the at least one sample inlet channel includes its own substantially planar surfaces oriented substantially parallel to the two substantially planar surfaces of the interior space.

In one embodiment, the magnetic field gradient generator includes a plurality of ferromagnetic elements patterned on the sorting device proximate the sorting station. In another embodiment, the magnetic field gradient generator includes a permanent magnet proximate the plurality of ferromagnetic elements. In yet another embodiment, the plurality of ferromagnetic elements are disposed within a fluid pathway of the sorting station to allow fluid contact between the ferromagnetic elements and the sample stream. The ferromagnetic elements can include micropatterned nickel elements. In one embodiment, the magnetic field gradient generator is configured to temporarily capture the magnetic particles and then release the magnetic particles.

Another embodiment is a method of capturing a target species in a sample, the method including: (a) providing the sample to at least a first inlet channel of a fluidic sorting device, where the sample includes magnetic particles having a specific affinity for the target species; (b) providing a sheath flow stream to the fluidic sorting device to produce one or more sheath streams that form a sheath around a sample stream within the fluidic separating device, and thereby reduce nonspecific binding of sample to the device; (c) magnetizing a magnetic field gradient generator to trap at least some of the magnetic particles and thereby separate the trapped magnetic particles from the sample; and (d) analyzing target species that are or were bound to the trapped the magnetic particles. In one embodiment, the magnetic field gradient generator includes a plurality of ferromagnetic elements. The ferromagnetic elements can include micropatterned ferromagnetic material on the fluidic device. In one embodiment, magnetizing the magnetic field gradient generator includes applying an external magnetic field from a permanent magnet or an electromagnet to the magnetic field gradient generator.

Methods can further include any combination of: 1) detecting the purified target species bound to the trapped magnetic particles, 2) amplifying a nucleic acid of the target species in the fluidic sorting device, 3) lysing cells in the fluidic sorting device, where at least some of the cells include the target species, 4) separating genetic material from cells or viruses in the fluidic sorting device, where at least some of the cells or viruses include the target species, and 5) recovering purified target species including at least 50% of the target species in the sample.

Another embodiment is a method of purifying a target species in a sample including magnetic particles having an affinity for the target species, the method including: (a) flowing the sample to into a fluidic sorting device having a magnetic field gradient generator to thereby capture at least some of the magnetic particles, where the flowing sample is contained with or sandwiched between a sheath of liquid that is substantially free of the sample; (b) removing or reducing a magnetic field applied to the magnetic field generator to thereby release captured magnetic particles; and (c) collecting or processing purified target species with at least some of the magnetic particles downstream from the magnetic field generator.

Another embodiment is a sheath flow device including: (a) a first laminar flow establishing surface upstream of a sheath flow plane area; (b) a sample laminar flow establishing surface parallel to the sheath flow plane area and upstream of a sample sheath flow plane area; and optionally, (c) a second laminar flow establishing surface upstream of a second sheath flow plane area. In one embodiment, the sheath flow device further includes a particle trapping station. This trapping station can be, for example, a magnetic trapping station. The sheath flow devices described herein can be part of a larger fluidic circuit.

Another embodiment is a sheath flow device including: (a) a first laminar flow establishing surface upstream of a sheath flow plane; (b) a sample laminar flow establishing surface parallel to the sheath flow plane area and upstream of a sample sheath flow plane area; and (c) a second laminar flow establishing surface upstream of a second sheath flow plane area. In one embodiment, the laminar flow establishing surfaces in (a) (b) and (c) are sufficient to maintain separate sheath flow planes substantially free of turbulent flow. In one embodiment, the sample laminar flow establishing plane of subpart (b) has a top and a bottom surface, and the second laminar flow surface of subpart (c) is a located on the surface opposite that used for sample laminar flow. The sheath flow device can be oriented substantially orthogonally with respect to a horizon. The sheath flow device can further include a particle trapping station. In one embodiment, the particle trapping station includes a ferromagnetic component. The sheath flow device can be adapted for magnetophoretic particle separation.

The sheath flow devices described herein can: further include at least one reservoir containing a reagent, be adapted for stem cell isolation from whole blood and/or be configured for microfluidic operation. In one embodiment, the sheath flow device includes a reservoir containing a reagent, the reagent including at least one of a buffer, a quantity of magnetic beads, a stem cell expansion agent, an aptamer, a composition including a protein, a bacterial cell culture, and a composition including a bacteriophage population.

Another embodiment is a method of separating a target species from a fluid sample in a sheath flow device, including: (a) pre-labeling the target species in the fluid sample with magnetic particles using a reagent bound to the magnetic particles that selectively binds the target species; (b) establishing a laminar buffer flow along a planar surface of the sheath flow device; (c) establishing a laminar flow of the fluid sample adjacent to the laminar buffer flow; (d) pulling the target species from the laminar flow of the fluid sample through the laminar buffer flow; and (e) trapping the target species on a magnetic trapping station. In one embodiment, the laminar flow is on the order of microns in height and on the order of millimeters in width. The buffer and sample laminar flows are adjacent by virtue of their area along the length and width dimensions being coincident, that is, they are stacked in the height dimension. One way to increase throughput when isolating target species using such methods is to increase the width of the laminar flows, while keeping the height of the flows in the micron (sub-millimeter) regime. This can be accomplished by running multiple sheath flow devices in parallel and/or by increasing the width of the laminar flow in the sheath device. In one embodiment, the method further includes establishing a second laminar buffer flow, adjacent to the first laminar buffer flow, before establishing the fluid sample laminar flow, where the laminar flow of the fluid sample is established between the first and second laminar buffer flows. In one embodiment, the first and second buffer laminar flows and the laminar flow of the fluid sample are sufficient to maintain separate flow planes substantially free of turbulent flow. In another embodiment, the magnetic trapping station comprises a ferromagnetic component. In one embodiment the target species comprises at least one of a cell, a bacterium, a virus, a protein and a nucleic acid. In one embodiment, the target species is a circulating tumor cell and the fluid sample is whole blood.

Another embodiment is a method of analyzing a patient the method including: (a) receiving a sample including tumor cells from a patient; (b) separating the tumor cells from the sample by a separation method including: (i) labeling the sample with magnetic particles having a specific affinity for the tumor cells, thereby producing a labeled sample, (ii) passing the labeled sample through a fluidic device including a sorting region having a magnetic field gradient effective to deflect and/or trap the magnetic particles from the labeled sample and thereby separate the tumor cells from the sample, where the sample flows in a sheath of buffer solution to reduce nonspecific binding of the sample to the fluidic device; and (c) characterizing the tumor cells separated from the sample in (b). In one embodiment, the characterizing in (c) provides information for diagnosing a condition, screening for a clinical trial, assessing the effectiveness of a therapeutic treatment, and measuring the effectiveness of surgery. In another embodiment, the sample is a fluid sample taken from the patient. In one embodiment, the sample is not taken from a biopsy of the patient, for example, the sample is a blood sample. In one embodiment, the tumor cells are circulating tumor cells from a non-haematologic cancer. In another embodiment, the characterizing is a count of the tumor cells and/or a molecular characterization of the tumor cells. Molecular characterization, for example, is a genetic mutation in the tumor cells.

Another embodiment is a method of monitoring and, if appropriate, adjusting a patient's treatment regimen, the method including: (a) receiving a sample including tumor cells from a patient undergoing a first treatment regimen; (b) separating the tumor cells from the sample by a separation method including: (i) labeling the sample with magnetic particles having a specific affinity for the tumor cells, thereby producing a labeled sample, (ii) passing the labeled sample through a fluidic device including a sorting region having a magnetic field gradient effective to deflect and/or trap the magnetic particles from the labeled sample and thereby separate the tumor cells from the sample, where the sample flows in a sheath of buffer solution to reduce nonspecific binding of the sample to the fluidic device; and (c) characterizing the tumor cells separated from the sample in (b) to suggest a future treatment for the patient. In one embodiment, the first treatment regimen is a chemotherapy regimen. In one embodiment, the future treatment is a different chemotherapy regimen. In one embodiment, suggesting the future treatment for the patient includes predicting a future effectiveness of the first treatment regimen, in another embodiment, suggesting a future treatment for the patient includes identifying a second treatment regimen that is different than the first treatment regimen and accounts for a characteristic of the tumor cells not previously observed for the patient.

The method of monitoring and, if appropriate, adjusting a patient's treatment regimen, can further include: (d) receiving a sample including tumor cells from the patient after the patient has undergone the second treatment regimen; and (e) thereafter performing (b) and (c) on the sample and tumor cells received in (d).

Another embodiment is a method of providing cell based products, the method including: (a) receiving a sample including target cells; (b) separating the target cells from the sample by a separation method including: (i) labeling the target cells with magnetic particles having a specific affinity for the target cells, thereby producing a population of labeled cells in the sample, (ii) passing the sample through a fluidic device including a sorting region having a magnetic field gradient effective to deflect and/or trap at least a portion of the population of labeled cells from the sample and thereby separate the target cells from the sample, where the sample flows in a sheath of buffer solution to reduce nonspecific binding of the sample to the fluidic device; and (c) deriving a cell based product from the target cells separated from the sample in (b). In one embodiment, the method further includes treating the target cells separated from the sample in (b) to produce the cell based product. In one embodiment, the target cells are stem cells and treating the target cells including treating the stem cells to become an effective therapeutic agent. In one embodiment, treating the stem cells to become an effective therapeutic agent includes differentiating the stem cells to produce a more specific cell type. As with other methods described herein, the sample can be a fluid sample taken from a patient, for example, a blood sample.

In one embodiment, the method further includes characterizing the target cells separated from the sample in (b). The characterization can be a count of the target cells and/or a molecular characterization of the target cells. In one embodiment, the molecular characterization is a genetic sequence of the target cells.

EXAMPLES

Presented below are working and prophetic examples. Example 1 demonstrates the present device in magnetophoretically sorting rare cells from complex blood samples. Example 2 describes kit on chip embodiments of the invention. Examples 3-7 describe embodiments where biologics or chemicals are part of the sample fluids. Examples 8 and 9 describe embodiments where the devices of the invention are used for monitoring, for example monitoring of environmental processes and biopharmaceutical manufacturing, respectively. Example 10 describes using devices of the invention for point of care diagnostics. Example 11 demonstrates comparative enrichment of hematopoietic progenitor cells (HPC's) from human cord blood samples.

Example 1

Isolation of Rare Cells from Whole Blood, and Comparison to Device Without Sheath Flow This working example demonstrates that the present sheath flow devices establish a fluid layer substantially preventing non-specific binding of non-target blood cells to a magnetophoretic trapping station.

We have demonstrated the microfluidic separation to enrich extremely rare target cells in $10^6$ MNC's (mononuclear cells) and whole blood based on magnetic force, which is termed as Multi-stream Micro Magnetic Separator (M-MMS or MMS).

Figure 6A:
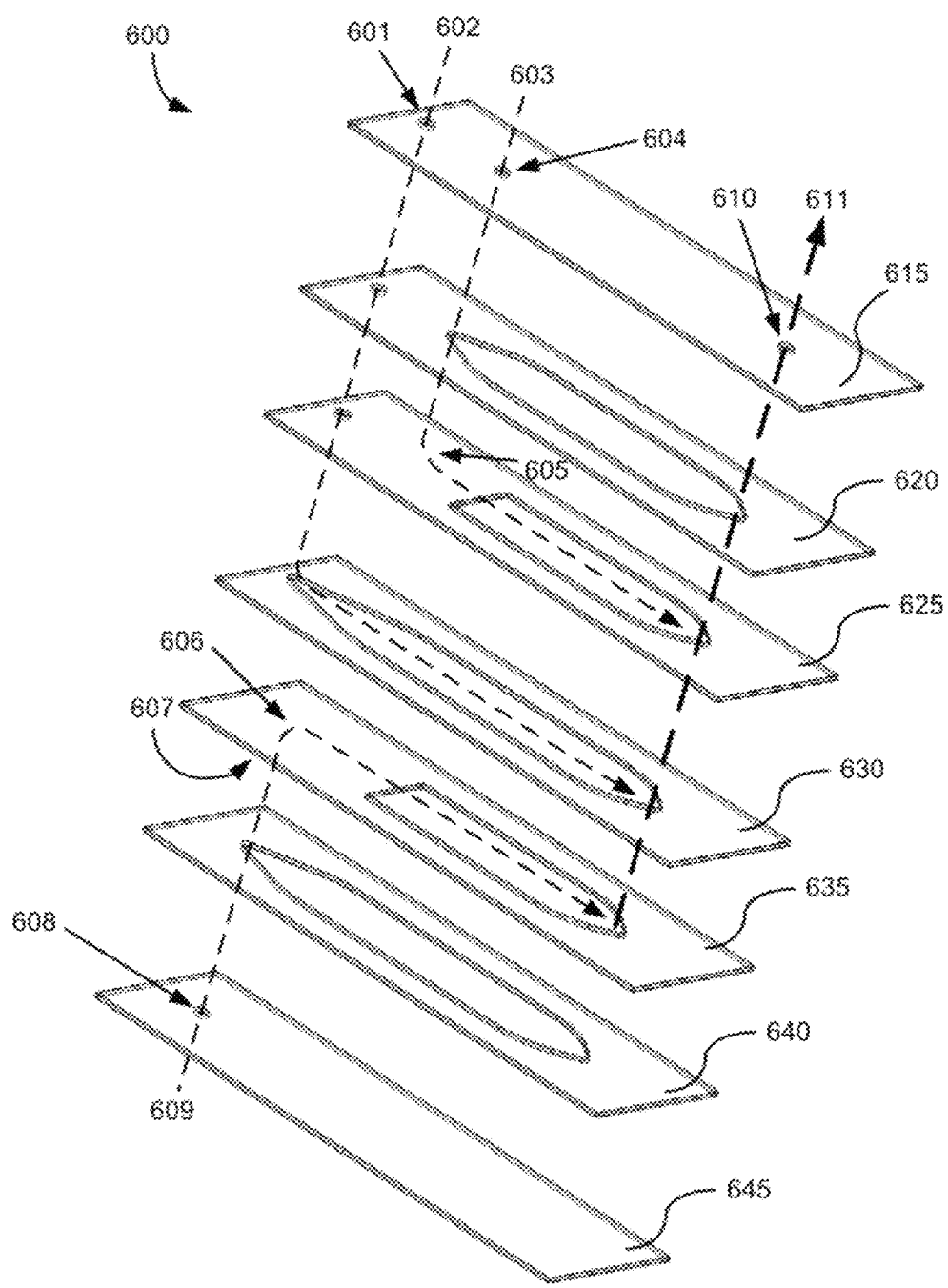
FIG. 6A is an exploded perspective illustrating components of a sheath flow device.
Figure 6B:
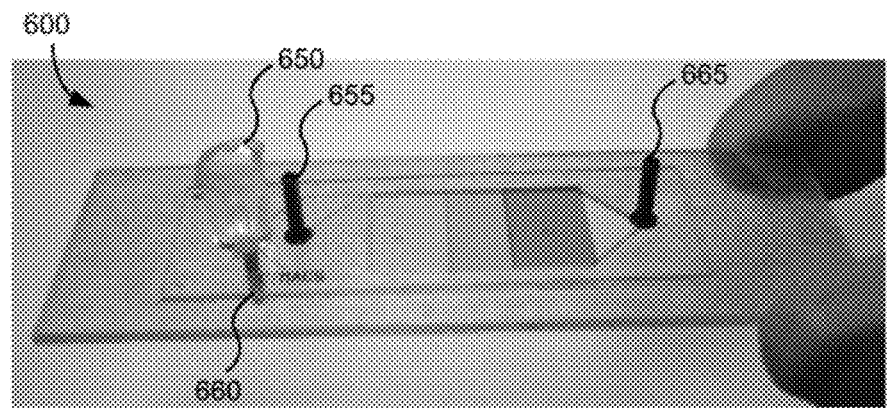
FIG. 6B is a photograph of the assembled sheath flow device of FIG. 6A.

The device illustrated in FIG. 6A and photographed in FIG. 6B was used. FIG. 6A is an exploded perspective illustrating one embodiment of sheath flow components of an MMS device, 600, of the present invention. The diagram is exploded for purposes of illustrating how individual components of the device, when registered with one another, create sheath flow. In this example, there are seven plates, 615, 620, 625, 630, 635, 640 and 645, each configured with access ports and/or channels, configured to create sheath flow when registered and buffer and sample flow are introduced to the device.

Sample inlet port, 601, is where liquid sample is introduced, as indicated by dashed arrow 602, showing the sample flow path. Sample flows through analogous ports in plates 620 and 625, and an end portion of a channel in plate 630, prior to striking area 606 (a sample laminar flow establishing surface) on the top surface (as illustrated) of plate 635. For convenience, sample flow arrow 602 is illustrated as if the flow is diverted by striking area 606 when registered, thus establishing a laminar flow in a direction parallel to and in the cavity in plate 630. Similarly, buffer inlet port 604 is where buffer solution is introduced, as indicated by dashed arrow 603, showing one buffer flow path. Buffer flows through an analogous end portion of a channel in plate 620, prior to striking area 605 (a buffer laminar flow establishing surface) on the top surface (as illustrated) of plate 625. For convenience, buffer flow arrow 603 is illustrated as if the flow is diverted by striking area 605, thus establishing a laminar flow in a direction parallel to and in the cavity in plate 625. Also similarly, another buffer inlet port 608 is where buffer is introduced, as indicated by dashed arrow 609, showing another buffer flow path. Buffer flows through an analogous end portion of a channel in plate 640, prior to striking area 607 (a buffer laminar flow establishing surface) on the bottom surface (as illustrated) of plate 635. For convenience, buffer flow arrow 609 is illustrated as if the flow is diverted by striking area 607, thus establishing a laminar flow in a direction parallel to and in the cavity in plate 635.

Arrow 611 depicts a common waste flow path as flows 602, 603 and 609 form a confluence at the distal end of the channels in plates 620, 625, 630, 635 and 640 (when registered) and exit the device via exit port 610 as indicated by dashed arrow 611.

Referring to FIG. 6B, a thin layer of nickel grid is patterned on the top surface of the channel (e.g., as described in relation to FIGS. 2A and 2B; seen in FIG. 6B as the grid pattern in shades of gray). The nickel grid is configured to generate a strong magnetic field gradient with the presence of external magnets and thus permit the capture of magnetic beads labeled target analytes. The unlabeled, background cells are not affected by the magnetic field gradient and are continuously eluted as waste. Since initially only pure sheath flow contact the top surface, only magnetically trapped target analytes will be trapped on the top surface, with minimum non-specific binding to the surface, resulting in extremely high purity samples. FIG. 6B shows sample inlet fitting, 650, for example a leurlock, upper and lower buffer inlet fittings, 655 and 660, respectively, and waste outlet fitting 665. These fittings allow, for example, sample to be introduced via syringe, while buffer is continually pumped into device 600 via dedicated lines. Waste is removed, for example, to a central reservoir via a dedicated waste line. Devices can be switched out by simply disconnecting the lines and reconnecting to a new device.

Figure 6C:
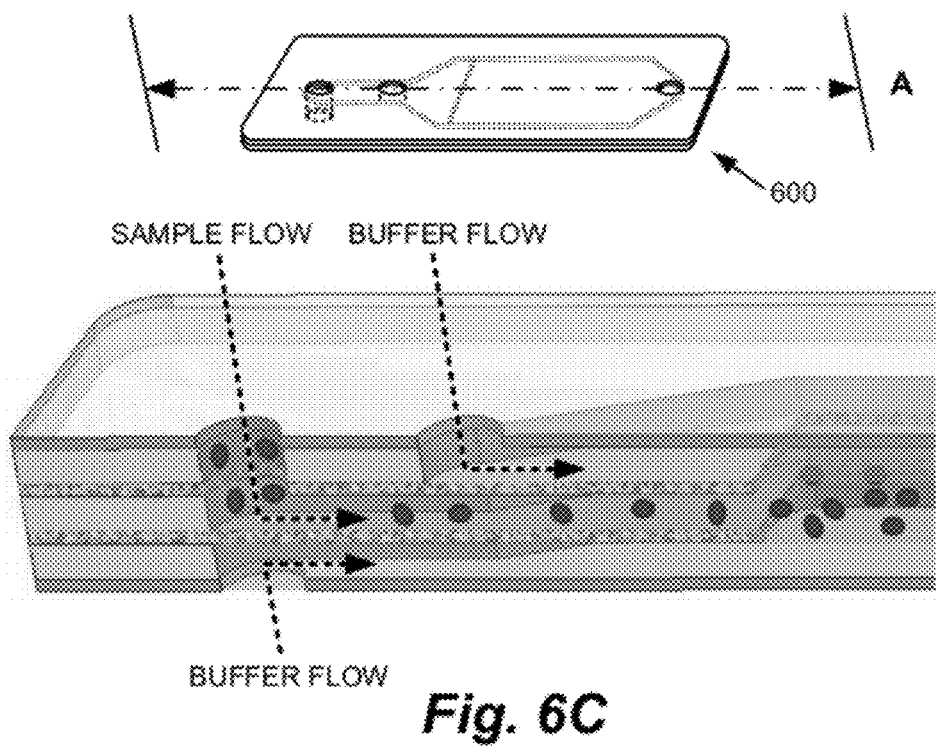
FIG. 6C is a perspective cross section illustration showing details of the sheath flow device described in FIGS. 6A and 6B.

FIG. 6C shows a cross section, A, of a portion (upper left quadrant) of device 600. The bottom portion of FIG. 6C, the expanded cross section, shows sample and buffer flow paths, how they are established adjacent to each other, and how the sample flow is prevented from touching the top and bottom inner surfaces of the sheath flow device 600. On the rightmost portion of the cross section the sheath of laminar buffer flow above and below the laminar sample flow is illustrated (dashed arrows indicate flow direction for each of top buffer, sample and bottom buffer.

Figure 7A:
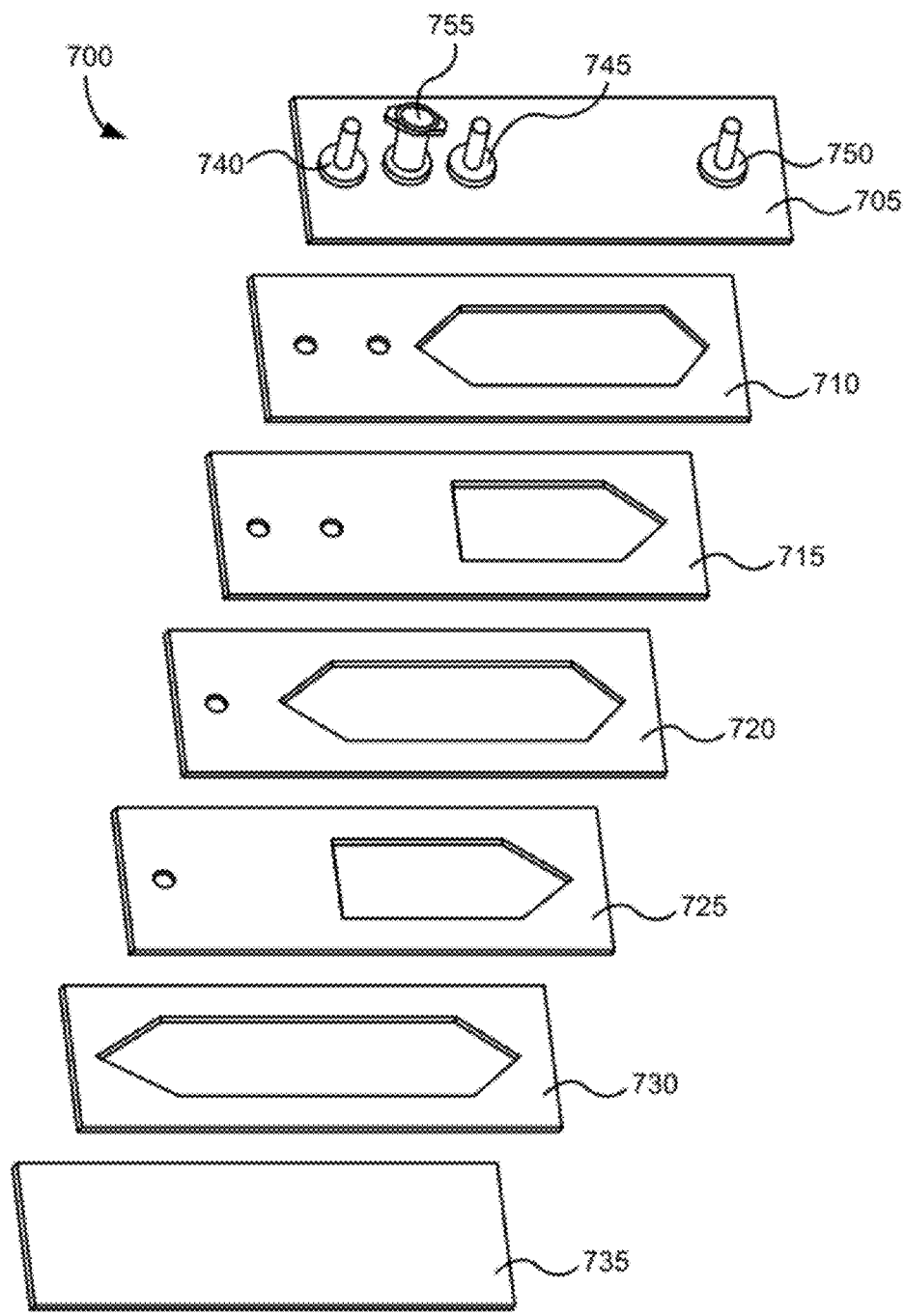
FIG. 7A is an exploded perspective illustrating components of a sheath flow device.
Figure 7B:
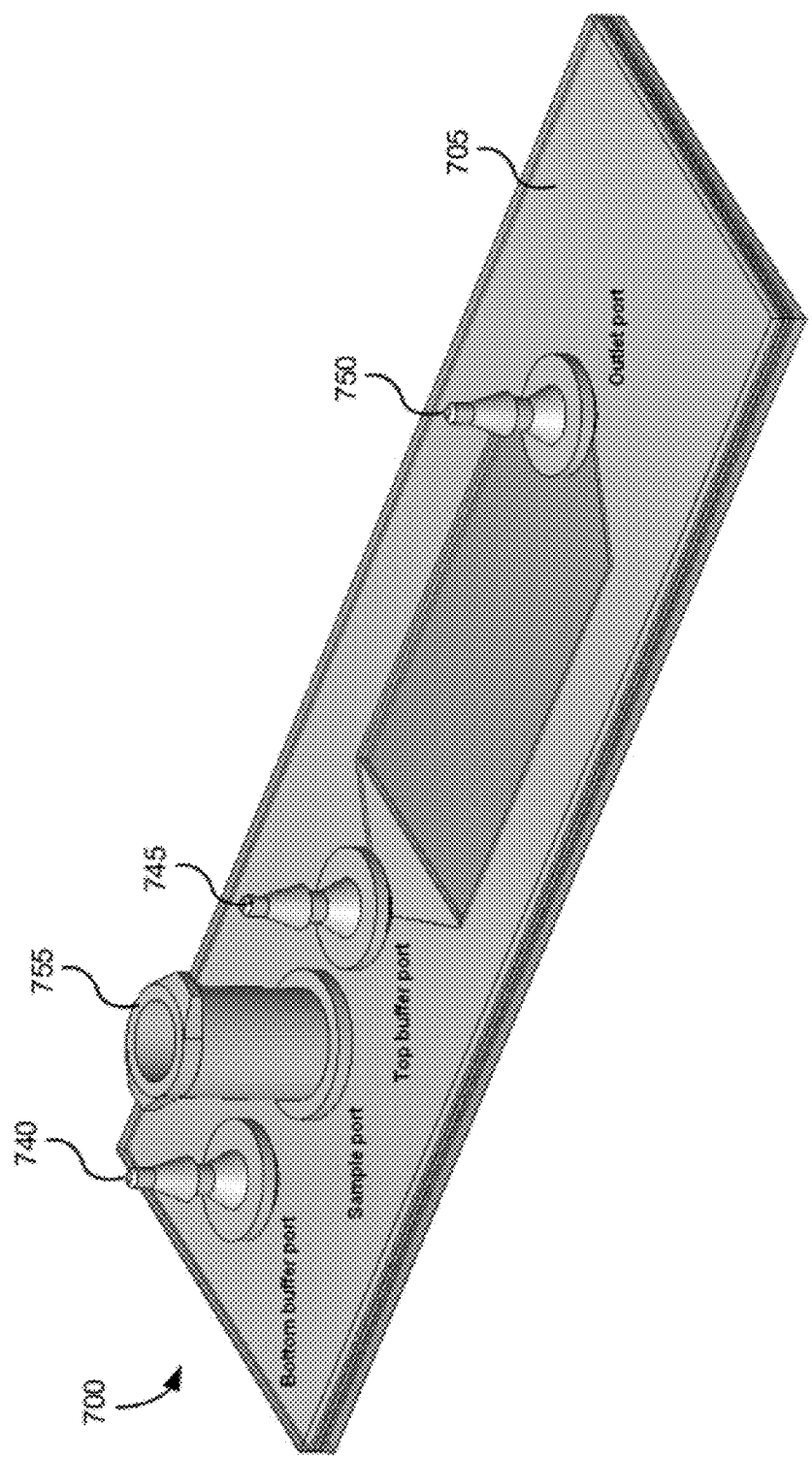
FIG. 7B is a perspective of the assembled sheath flow device depicted in FIG. 7A.

FIG. 7A is an exploded perspective illustrating components of a similar sheath flow device, 700. Sheath flow device 700 has layers 705, 710, 715, 720, 725, 730 and 735, which when registered adjacent to each other in a stack as depicted, form device 700. Device 700 differs from device 600 because device 700 has all the inlets (lower buffer inlet, 740, upper buffer inlet, 745, and sample inlet, 755) and outlet (waste outlet 750) on top plate 705 (recall device 600 had a lower buffer inlet on the bottom plate). This allows for convenient handling, since device 700 can be positioned on a flat surface during operation. In this example, top plate 705 is glass with a nickel trapping grid, layers 710, 720 and 730 are adhesive layers, for example, about 0.2 mm thick, layers 715 and 725 are polycarbonate, for example, about 0.125 mm thick, and layer 735 is glass. FIG. 7B is a perspective of the assembled sheath flow device 700 depicted in FIG. 7A.

The present sheath flow device was configured such that the bottom fluid layer was matched the viscosity and density of blood, with 50% (w/w) sucrose.

Figure 4:
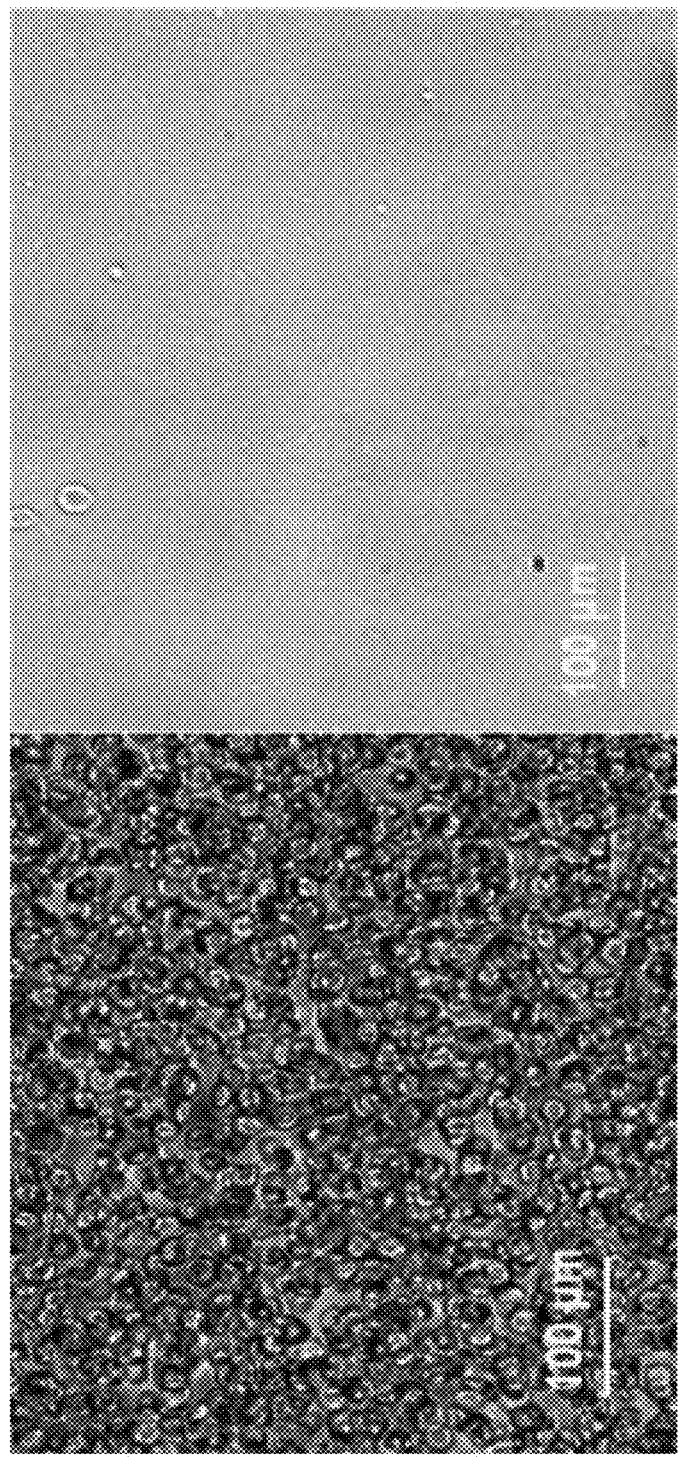
FIG. 4 is a reproduction of photographs illustrating the non-specific binding of blood cells on a solid microfluidic channel surface in a device without sheath flow (left panel) and then using sheath flow (right panel).

Sheath flow efficacy was first demonstrated by injecting whole blood (in the absence of magnetic particles), at equal flow rates, in the chip with and without sheath flow for comparison. As shown in FIG. 4 (left panel), without sheath flow RBC's and other cells nonspecifically attached to the surface. In FIG. 4 (right panel) the sheath flow device demonstrated efficacy because the surface is substantially free of non-target cells.

Figure 5A:
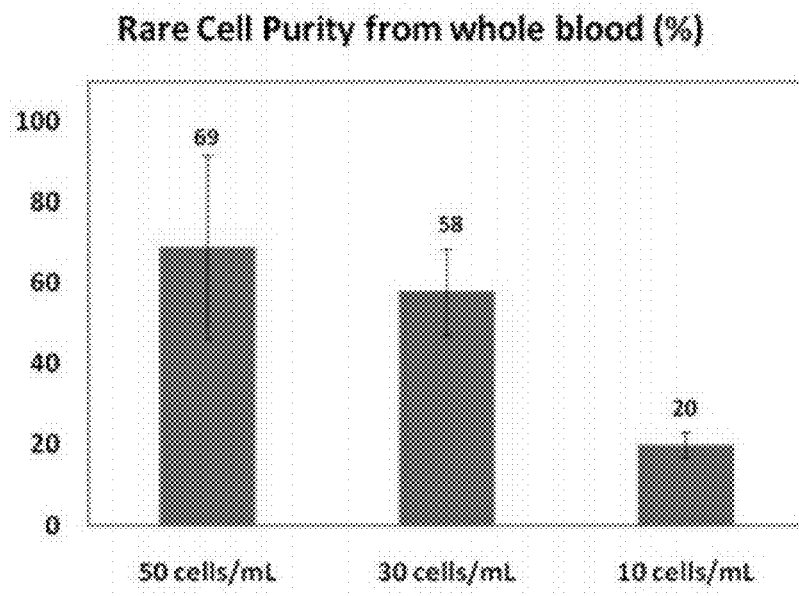
FIGS. 5A and 5B are graphs illustrating rare cell purity and rare cell recovery, respectively, from whole blood using sheath flow devices as described herein.
Figure 5B:
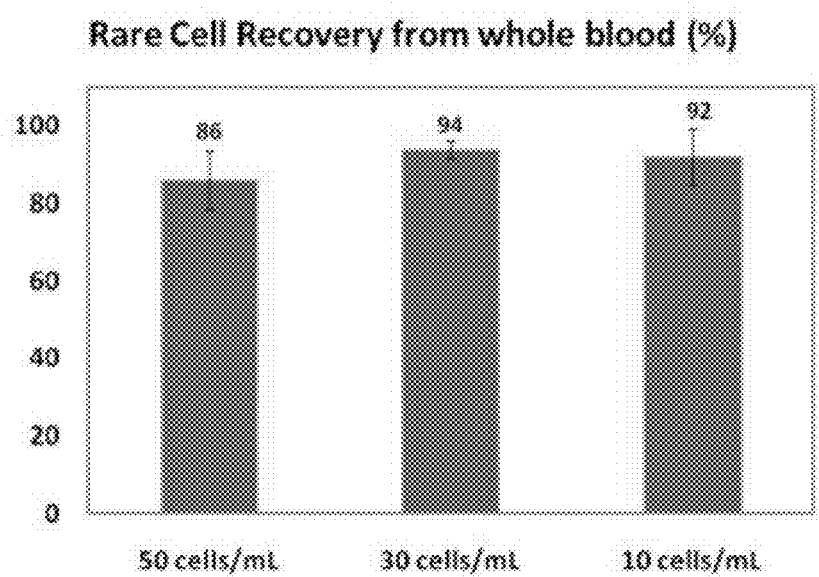

To quantify M-MMS ability to recover and retrieve rare cells, MCF-7 breast cancer cells were pre-labeled with commercially available nano-sized magnetic particles (anti-PE magnetic particles, BD Biosciences). Pre-labeled MCF-7 tumor cells were spiked into whole blood at 50 cells/ml, 30 cells/ml or 10 cells/ml. The results are presented in the graphs in FIGS. 5A and 5B. The average purity is 69%, 58% and 20% (for 50, 30, and 10 cells/ml respectively (5A)). This is around $1 \times 10^7$ fold enrichment over the initial sample. The average cell recovery is 86%, 94% and 92% (for 50, 30 and 10 cells/ml respectively (5B)).

Using in-situ labeling, about 90% recovery of target cells was achieved. The cell purity is about 13%, which is $2 \times 10^6$ fold enrichment of the initial sample. Presumably this was not as efficient as pre-labeled sorting because of the inefficiencies related to in situ magnetic labeling.

As such, the present invention provides fluidic sheath flow devices including a first fluid layer of laminar sheath flow in a plane adjacent to and parallel with a sample fluid layer in a laminar flow plane, and, optionally, a second fluid layer of laminar sheath flow adjacent to a second side of the sample fluid in a laminar flow plane, where sheath flow is established first on a solid support.

Example 2

"Kit on a Chip"

This is a prophetic example. A sheath flow device of the present invention is manufactured, according to a predefined fluidic circuitry. The device is manufactured using fluid dispensing automation instrumentation to pre-fill selected reservoirs with desired fluids. The reservoirs are sealed, with a portion of the pre-filled reservoir having a seal that will burst with predetermined tensile force, such that the fluid is in fluid communication with a different reservoir. There are several reservoirs prefilled for a particular purpose, and fluid circuitry allows the fluids to flow to a predetermined area upon application of suitable force, such as pneumatic force. Thus, sheath flows of the instant invention are achieved via fluid leaving reservoirs and entering devices of the instant invention, e.g. as described in FIGS. 1 and 2, which are part of the predefined fluidic circuitry. In one example, automated instrumentation applies force with pneumatic pistons in a predetermined temporal pattern coordinating with the fluidic circuitry of the device to create sheath flows.

Example 3

Biomarker Detection

This is a prophetic example. A sheath flow device of the present invention is configured with fluidic circuitry for sorting a biomarker from a biological fluid obtained from an individual. The biomarker presence indicates a particular disease state. The biomarker is selected from among a cell, a protein, a nucleic acid, or a degradation product of any of the above. The disease state is selected from among a cancer, a neurological disease, and an infection. The cancer biomarker is selected from among a circulating tumor cell, a protein, and a nucleic acid. The neurological disease biomarker is selected from among a cell, a protein including but not limited to an abeta 1-42 protein or fragment or oligomer thereof, or other biomarker for a neurological disease selected from among Alzheimer's disease, Huntington's disease, Amylateral sclerosis ("ALS" or Lou Gehrig's disease), a dementia, multiple sclerosis, and a disease caused by a prion. The biomarker for infection is selected from an infectious agent and a secondary pathogen or detectable marker of deleterious effect, and includes, but is not limited to, a virus, bacteria, a fungus, a prion and any other type of infectious agent. The virus may be an HIV virus, a hepatitis virus (of any type), a flu virus (of any type), a papilloma virus (HPV) of any type, a rabies virus, or any other viral infectious agent. The biomarker may be a portion of the organism or infectious agent so listed. For example, the biomarker may be a protein associated with a viral coat.

Example 4

Aptamer Screening

This is a prophetic example. A sheath flow device of the present invention is configured with fluidic circuitry for use of an aptamer for detection of a rare molecule in a fluid sample. The aptamer is optionally associated with a detectable marker. The aptamer is exposed to a fluidic suspension under conditions for it to bind to its target. The aptamer and target are captured in a trapping station located within a reservoir in the present sheath flow device. Non-target material is washed away with fluid (e.g., buffer) applied using pneumatic (or other force) force insufficient to dislodge the aptamer/target from the trapping station. This prophetic example may be used, for instance, to detect substances in urine, blood, or other bodily fluid. For example, one may detect trace amounts of cocaine or other illicit ingested pharmacological agents in urine. See, e.g., Swensen, J. S. et al. Continuous, real-time monitoring of cocaine in undiluted blood serum via a microfluidic, electrochemical aptamer-based sensor. *J. Am. Chem. Soc.* doi:10.1021/ja806531z (2009), herein incorporated by reference for all purposes.

Example 5

Testing for Analytes in Body Fluid

This is a prophetic example. A sheath flow device of the present invention is configured for fluidic circuitry so that an individual (such as a human or animal) may be monitored for drug, illicit or not, presence or dosages. The present devices may be configured to detect or monitor medically prescribed dosages, pharmacokinetic, body or brain performance enhancing, illicit (methamphetamine, cocaine, marijuana (cannabinoids)) or endocrine related, such as glucose (insulin). For example, a sheath flow device of the present invention is configured to provide prefilled reservoirs (or chambers) with reagents suitable for detecting pharmaceutical or pharmaceutical degradation or downstream metabolic agents, in a bodily fluid, such as blood or urine. A sheath flow device is configured so that a blood (for example) sample is dispensed into a reservoir, and reservoirs pre-filled with suitable reagents are then permitted to open with applied force, such as manual tensile pressure. The reagents when so combined with the bodily fluid provide a visible detection of whether the patient is properly dosed.

Example 6

Chemical Library Screening, Including Aptamer

This is a prophetic example. A sheath flow device of the present invention is configured with fluidic circuitry for screening a library of chemicals for a particular purpose. For example, a library of aptamers may be screened against a protein target, such as by using a phage display. The aptamer/protein complexes may be analyzed to identify the aptamers so binding, and any binding characteristics, and the enriched aptamers may be subjected again to library screening. This may be performed in an iterative process to select aptameric moieties with particular characteristics, such as binding affinities or binding to particular epitopes on a protein moiety for example. A sheath flow device of this example will have a reservoir for holding, and optionally culturing a phage display population of a predetermined protein, and inlet port or a prefilled chamber with the subject aptameric library to be so screened. Alternatively, one may have a reservoir holding an aptameric library to which is dispensed a desired protein (or other substrate for selection). The binding reaction may be aided with force applied to a reservoir to admix the aptamer library and protein (or other source).

Example 7

Genome Screening; DNA Analysis

This is a prophetic example. A sheath flow device of the present invention is configured with microfluidic circuitry and used in nucleic acid sorting. A sample of DNA is either placed within the device, or cells containing DNA are placed within the device, in fluid communication with reservoirs and channels for delivering reagents suitable to bind to particular DNA sequences (and optionally lyse cells to expose internal DNA if so desired or required). For example, DNA primers are used to bind to specific corresponding DNA sequences.

The primers are applied to the reservoir containing the subject DNA (such as a genome or forensic sample). A wash fluid is added to the chamber to wash away unbound moieties. The primer/DNA is then exposed to several rounds of polymerase chain reaction, including applying reagent. The reagents are suitably mixed using automated instrumentation for applying tensile strength.

Example 8

Environmental Monitoring

This example is a prophetic example. A sheath flow device of the present invention is configured with suitable materials and fluidic circuitry for environmental monitoring or analysis. While environmental fluid sample processing has much in common with aqueous fluid processing from biological fluids (above), modifications for field use include rugged material (e.g., made to withstand extremes in temperature, sunlight, salinity, or other environmental conditions), and use in the absence of reliable electricity. For example, a homeowner may wish to monitor drinking water, but collecting drinking water in a subject over a period of time, and analyzing once. Or, the present sheath flow devices can be used for monitoring microbial species indicators for oil and gas drilling, where certain species are known to be associated with particular oil or gas containing geologic formations. Thus, one of ordinary skill in the art selects materials able to withstand sample application under these conditions. Sheath flow devices of the invention can be further configured so that manual (hand or hand-held tool) applied pressure is sufficient for fluidic flow in the sheath flow path. Drinking or environmental water (such as saline or fresh water sources), soil (such as soil remediation), PCB or superfund site clean-up monitoring, environmental radiation monitoring, repopulation (such as algae or krill) or other ecological purposes, as well as residential environmental monitoring (such as water, air or soil sample monitoring or analysis, including drinking or swimming pool water). One may use a prefilled device containing aptamers (for example, or other selective binding molecules) that selectively bind to heavy metals, such as mercury, lead, iron, or even gold or silver (for prospecting). One may monitor environmental toxins, such as arsenic, undue pharmaceutical environmental contamination, MBE's or other organic solvents. Acidification of oceanic areas, such as the continental shelf areas, may be performed with the inclusion of acidification indicators (e.g., colorimetric strips) for example.

Example 9

Monitoring Biopharmaceutical Manufacturing

This is a prophetic example. The present sheath flow devices may be used in the manufacture of biologicals for monitoring during the biological process. For example, one may collect protein from a separate bioreactor at various stages to monitor protein production for lot-to-lot variation. Vaccine manufacturing may also be monitored in this way. A variety of biologicals and biopharmaceutics can be monitored for quality assurance purposes using the present sheath flow devices.

Example 10

Point of Care, Diagnostic

This is a prophetic example. The present sheath flow devices are configured suitably for various point of care blood panel analyses typically performed in a clinical laboratory. The present sheath flow devices are configured so that a patient's blood is first deposited into a reservoir, and then, using tensile pressure, directed to flow to be partitioned in separate reservoirs. The blood sample so partitioned into individual reservoirs is then separately exposed to moieties used in such clinical laboratory practice, such as stains or dyes, or antibodies. Alternatively or additionally, the blood so partitioned may be exposed to alternative reagents better suited for the intended purpose, such as liver enzyme, blood sugar, thyroid, protein C or other blood moieties.

Example 11

Comparative Enrichment of Hematopoietic Progenitor Cells (HPC's) from Human Cord Blood Samples The example device of the invention, as described in Example 1 above employing sheath flow and magnetic trapping, was compared on a side-by-side basis with a commercially available MACS® Cell Separation Column (available from Miltenyi Biotec of Bergisch Gladbach, Germany), a device for cell separation employing magnetic trapping of cells labeled with magnetic particles, but without sheath flow capability.

Frozen or 2-day old fresh cord blood multinucleate cells (MNC's) were first filtered to remove any dead cells. The sample was then labeled with Miltenyi CD34 Microbeads (available from Miltenyi Biotec of Bergisch Gladbach, Germany. The labeled sample was divided and one portion was run through the Miltenyi separation column described above and the other portion was run through the sheath flow magnetic separation device of the invention as described, for example, in relation to Example 1. The a portion of the sample run through the Miltenyi column was run again through another Miltenyi column so that a comparison of one pass (MACS 1x) and two passes (MACS 2x) through the Miltenyi system could be compared to a single pass through the sheath flow device (MMS) of the invention. Each of the three purified samples was analyzed using standard immuno-fluorescence staining and FACS analysis as one of ordinary skill in the art would appreciate.

Figure 9A:
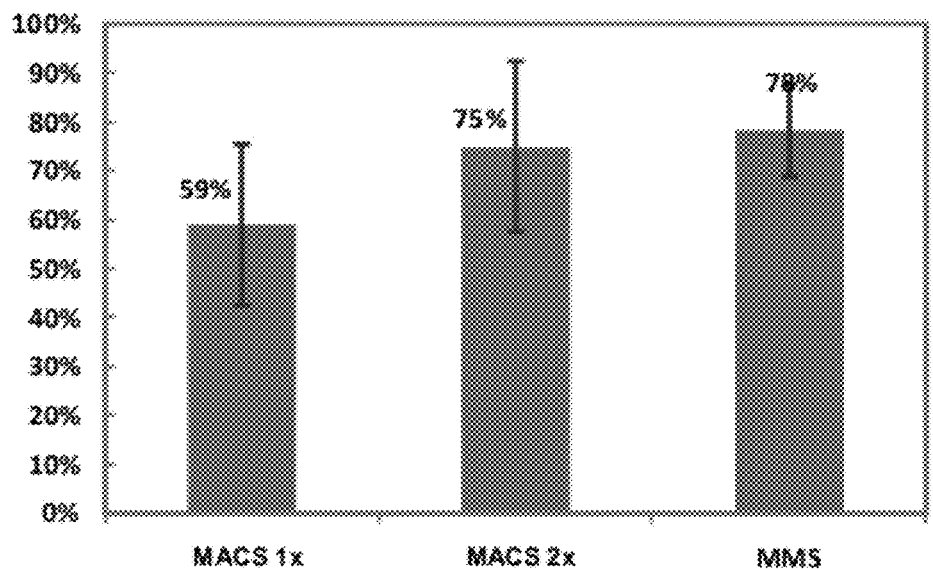
FIGS. 9A and 9B show purity and recovery of hematopoietic cells isolated from cord blood using a sheath flow device as described herein.
Figure 9B:
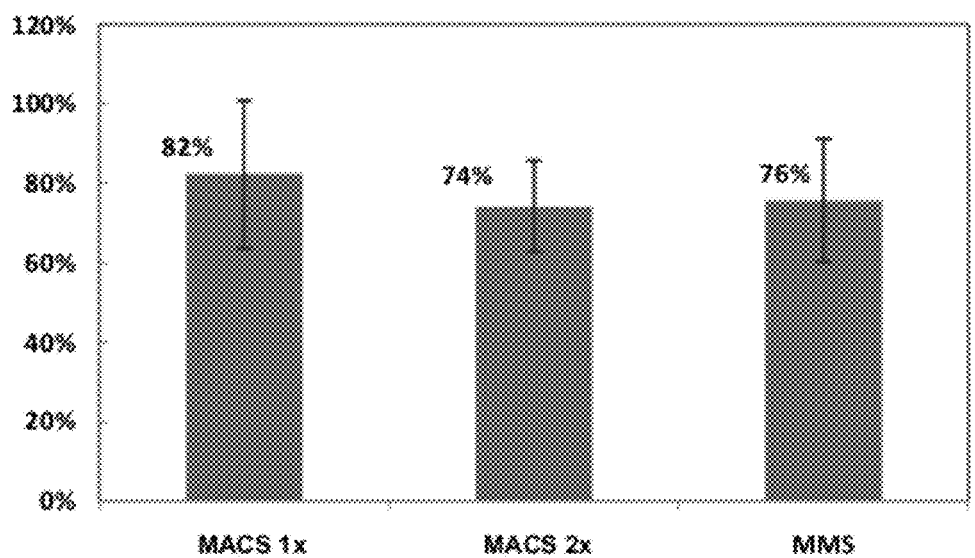

FIGS. 9A and 9B show the results of the FACS analysis of HPC's isolated using the above described methods, MACS 1x, MACs 2x and MMS, respectively. The data is compiled for N=6 runs as described above, with error bars included to show standard deviation. FIG. 9A shows that the HPC purity from the MMS separation is much better than MACS 1x and perhaps better but at least comparable to MACS 2x. This demonstrates the improved capabilities of the MMS technology over conventional, non-sheath flow, devices. FIG. 9B shows that HPC recovery based on each of MACS 1x, MACS 2x and MMS, respectively. Although the MACS 1x showed higher recovery, the samples were of lower purity (see FIG. 9A) than that of MACS 2x or MMS. The results also show that recovery (and purity) with MMS is comparable to MACS 2x, but with only a single pass through the MMS device as compared to double elution with the MACS conventional device to achieve the equivalent purity and recovery.

There are a wide variety of configurations and applications, and one of ordinary skill in the art will ascertain these in view of the present disclosure. The present invention is not limited by the specific examples described herein.

What is claimed is:

1. A sheath flow device comprising:
   (a) a first laminar flow establishing surface upstream of a sheath flow plane area configured to establish a sheath laminar flow in the sheath flow plane area;
   (b) a second laminar flow establishing surface parallel to the sheath flow plane area and upstream of a sample sheath flow plane area, wherein the second laminar flow establishing surface is configured to establish a sample laminar flow in the sheath flow plane area; and
   (c) a particle movement station configured to deflect a target species from the sample laminar flow and into the sheath laminar flow, wherein the particle movement station has a substantially rectangular interior space for bounding the sample laminar flow and the sheath laminar flow, wherein the interior space has first and second lateral dimensions transverse to the sample laminar flow, wherein the second lateral dimension is at least about 2 times larger than the first lateral dimension such that nonspecific binding is reduced along the larger of the first and second lateral dimensions.

2. The sheath flow device of claim 1, further comprising (d) a third laminar flow establishing surface upstream of a second sheath flow plane area.

3. The sheath flow device of claim 2, wherein the laminar flow establishing surfaces in (a) (b) and (d) are sufficient to maintain separate sheath flow planes substantially free of turbulent flow.

4. The sheath flow device of claim 3, further comprising a structural member having a first surface and a second surface, wherein the first surface and the second surface are opposite each other, wherein the first surface comprises the second laminar flow establishing surface of subpart (b), and wherein the second surface comprises the third laminar flow establishing surface of subpart (d).

5. The sheath flow device of claim 4, wherein the particle movement station employs at least one of a magnetic force, an acoustic force, an electrophoretic force and an optical force.

6. The sheath flow device of claim 5, adapted for magnetophoretic particle separation of a target species.

7. The sheath flow device of claim 6, further comprising at least one reservoir containing a reagent.

8. The sheath flow device of claim 6, wherein the target species is a stem cell and the sample laminar flow comprises whole blood.

9. The sheath flow device of claim 6, that is microfluidic.

10. The sheath flow device of claim 6, further comprising a reservoir containing a reagent, said reagent comprising at least one of a buffer, a quantity of magnetic beads, a stem cell expansion agent, an aptamer, a composition comprising a protein, a bacterial cell culture, and a composition comprising a bacteriophage population.

11. A method of separating a target species from a fluid sample in a sheath flow device, comprising:
    (a) providing the device of claim 1;
    (b) establishing a laminar sheath of buffer flow along a planar surface of the sheath flow device;
    (c) establishing a laminar flow of the fluid sample adjacent to the laminar sheath of buffer flow; and
    (d) deflecting the target species from the laminar flow of the fluid sample and into the laminar sheath of buffer flow; wherein the laminar sheath of buffer flow and the laminar flow of the fluid sample are adjacent.

12. The method of claim 11, further comprising establishing a second laminar sheath of buffer flow, adjacent to the laminar flow of the fluid sample, wherein (b) comprises establishing the laminar flow of the fluid sample between the first and second laminar buffer flows.

13. The method of claim 12, wherein establishing the first and second laminar sheaths of buffer flow and the laminar flow of the fluid sample are sufficient to maintain separate flow planes substantially free of turbulent flow.

14. The method of claim 13, wherein deflecting the target species from the laminar flow of the fluid sample and into the laminar sheath of buffer flow comprises using at least one of a magnetic force, an acoustic force, an electrophoretic force and an optical force.

15. The method of claim 14, wherein the target species comprises at least one of a cell, a bacterium, a virus, a protein and a nucleic acid.

16. The method of claim 15, wherein the targets species is isolated in a trapping station over which the laminar sheath of buffer flow passes.

17. The method of claim 16, wherein the trapping station employs magnetic force in order to trap the targets species selectively labeled with magnetic particles.

18. The method of claim 17, wherein the target species is a circulating tumor cell and the fluid sample is whole blood.

19. A method of analyzing a patient the method comprising:
    (a) providing the flow device as recited in claim 1;
    (b) receiving a sample comprising tumor cells from a patient;
    (c) separating said tumor cells from the sample by a separation method comprising: (i) labeling the sample with magnetic particles having a specific affinity for said tumor cells, thereby producing a labeled sample, (ii) passing the labeled sample through the fluidic device comprising a sorting region having a magnetic field gradient effective to deflect and/or trap the magnetic particles from the labeled sample and thereby separate the tumor cells from the sample, wherein the sample flows in a sheath of buffer solution to reduce nonspecific binding of the sample to the fluidic device; and
    (d) characterizing the tumor cells separated from the sample in (c).

20. The method of claim 19, wherein the characterizing in (c) provides information for diagnosing a condition, screening for a clinical trial, assessing the effectiveness of a therapeutic treatment, and measuring the effectiveness of surgery.

21. The method of claim 19, wherein the sample is a fluid sample taken from the patient.

22. The method of claim 19, wherein the sample is not taken from a biopsy of the patient.

23. The method of claim 19, wherein the sample is a blood sample.

24. The method of claim 23, wherein the tumor cells are circulating tumor cells from a non-haematologic cancer.

25. The method of claim 19, wherein the characterizing is a count of said tumor cells.

26. The method of claim 19, wherein the characterizing is a molecular characterization of said tumor cells.

27. The method of claim 26, wherein said molecular characterization is a genetic mutation in said tumor cells.

28. A method of monitoring and, if appropriate, adjusting a patient's treatment regimen, the method comprising:
    (a) providing the flow device as recited in claim 1;
    (b) receiving a sample comprising tumor cells from a patient undergoing a first treatment regimen;
    (c) separating said tumor cells from the sample by a separation method comprising: (i) labeling the sample with magnetic particles having a specific affinity for said tumor cells, thereby producing a labeled sample, (ii)

passing the labeled sample through the fluidic device comprising a sorting region having a magnetic field gradient effective to deflect and/or trap the magnetic particles from the labeled sample and thereby separate the tumor cells from the sample, wherein the sample flows in a sheath of buffer solution to reduce nonspecific binding of the sample to the fluidic device; and (d) characterizing the tumor cells separated from the sample in (c) to suggest a future treatment for the patient.

29. The method of claim 28, wherein the first treatment regimen is a chemotherapy regimen.

30. The method of claim 29, wherein the future treatment is a different chemotherapy regimen.

31. The method of claim 28, wherein suggesting the future treatment for the patient comprises predicting a future effectiveness of the first treatment regimen.

32. The method of claim 28, wherein suggesting a future treatment for the patient comprises identifying a second treatment regimen that is different than the first treatment regimen and accounts for a characteristic of the tumor cells not previously observed for the patient.

33. The method of claim 32, further comprising:
(d) receiving a sample comprising tumor cells from the patient after the patient has undergone the second treatment regimen; and
(e) thereafter performing (b) and (c) on the sample and tumor cells received in (d).

34. A method of providing cell based products, the method comprising:
(a) providing the flow device as recited in claim 1;
(b) receiving a sample comprising target cells;
(c) separating said target cells from the sample by a separation method comprising: (i) labeling the target cells with magnetic particles having a specific affinity for said target cells, thereby producing a population of labeled cells in the sample, (ii) passing the sample through the fluidic device comprising a sorting region having a magnetic field gradient effective to deflect and/or trap at least a portion of the population of labeled cells from the sample and thereby separate the target cells from the sample, wherein the sample flows in a sheath of buffer solution to reduce nonspecific binding of the sample to the fluidic device; and
(d) deriving a cell based product from the target cells separated from the sample in (c).

35. The method of claim 34, further comprising treating the target cells separated from the sample in (b) to produce the cell based product.

36. The method of claim 35, wherein the target cells are stem cells and treating the target cells comprising treating the stem cells to become an effective therapeutic agent.

37. The method of claim 36, wherein treating the stem cells to become an effective therapeutic agent comprises differentiating the stem cells to produce a more specific cell type.

38. The method of claim 34, wherein the sample is a fluid sample taken from a patient.

39. The method of claim, 38, wherein the fluid sample is a blood sample.

40. The method of claim 34, further comprising characterizing the target cells separated from the sample in (b).

41. The method of claim 40, wherein the characterizing is a count of said target cells.

42. The method of claim 40, wherein the characterizing is a molecular characterization of said target cells.

43. The method of claim 42, wherein said molecular characterization is a genetic sequence of said target cells.

44. A fluidic separating device comprising:
(a) at least one sample inlet channel configured to provide a sample stream in the fluidic separating device;
(b) at least one sheath flow inlet channel configured to provide one or more fluid sheaths within the fluidic separating device and separating the sample stream from a surface of the device, thereby reducing nonspecific binding of components of the sample to the device; and
(c) a sorting station fluidly coupled to the sample and sheath flow inlets and located along a path of the sample stream, wherein the sorting station has a substantially rectangular interior space for bounding the one or more fluid sheaths, wherein the interior space has first and second lateral dimensions transverse to the sample stream's direction of flow, wherein the second lateral dimension is at least about 2 times larger than the first lateral dimension such that nonspecific binding is reduced along the larger of the first and second lateral dimensions, and wherein during operation the sorting station has a magnetic field gradient effective to deflect and/or trap magnetic particles from the sample stream.

45. The fluidic separating device of claim 44, wherein the at least one sheath flow inlet channel is configured to provide two sheath streams separated from one another by said sample stream along the first lateral dimension.

46. The fluidic separating device of claim 44, wherein the sorting station has a substantially rectangular interior space for bounding fluid flowing through the sorting station, and
wherein the interior space is defined, in part, by two substantially parallel and substantially planar surfaces separated by a distance not greater than about 2 millimeters, and
wherein the at least one sheath flow inlet channel is configured to provide two sheath streams flowing in contact with the two parallel planar surfaces and separated from one another by said sample stream.

47. The fluidic separating device of claim 46, wherein the two substantially parallel and substantially planar surfaces are separated by a distance not greater than about 1 millimeter.

48. The fluidic separating device of claim 46, wherein the at least one sheath flow inlet channel comprises a first sheath flow inlet channel, which comprises a substantially planar surface located upstream of the sorting station and oriented substantially parallel to the two substantially planar surfaces of the interior space.

49. The fluidic separating device of claim 48, further comprising a second sheath flow inlet channel, which comprises its own substantially planar surface located upstream of the sorting station and oriented substantially parallel to the two substantially planar surfaces of the interior space.

50. The fluidic separating device of claim 49, wherein the at least one sample inlet channel comprises its own substantially planar surfaces oriented substantially parallel to the two substantially planar surfaces of the interior space.

* * * * *